United States Patent
Lamberty et al.

(10) Patent No.: US 6,916,782 B1
(45) Date of Patent: Jul. 12, 2005

(54) GENE CODING FOR HELIOMICINE AND USE THEREOF

(75) Inventors: Mireille Lamberty, Strasbourg (FR); Philippe Bulet, Vendenheim (FR); Gary Brookhart, Durham, NC (US); Jules Hoffman, Strasbourg (FR)

(73) Assignee: Aventis Cropscience S.A., Lyon Cedex (FR)

(*) Notice: Subject to any disclaimer, the term of this patent is extended or adjusted under 35 U.S.C. 154(b) by 0 days.

(21) Appl. No.: 09/673,274

(22) PCT Filed: Apr. 12, 1999

(86) PCT No.: PCT/FR99/00843

§ 371 (c)(1),
(2), (4) Date: Feb. 2, 2001

(87) PCT Pub. No.: WO99/53053

PCT Pub. Date: Oct. 21, 1999

(30) Foreign Application Priority Data

Apr. 15, 1998 (FR) .............................. 98 04933

(51) Int. Cl.⁷ ............................................. A61K 38/02
(52) U.S. Cl. ........................ 514/2; 530/300; 530/350; 530/402; 435/440; 435/69.7; 514/12
(58) Field of Search ................. 514/2, 12; 530/300, 530/350, 402, 324; 435/440, 69.7, 69.1, 320.1; 536/23.1

(56) References Cited

U.S. PATENT DOCUMENTS 6,127,336 A 10/2000 Bulet et al.
6,465,719 B1 * 10/2002 DeRose et al. ............. 800/301

FOREIGN PATENT DOCUMENTS

| EP | 0307841 | 3/1989 |
| EP | 0607080 | 7/1994 |
| FR | 2695392 | 3/1994 |
| FR | 2725992 | 4/1996 |
| GB | 1355163 | 6/1974 |
| WO | 9011770 | 10/1990 |
| WO | 9730082 | 8/1997 |

OTHER PUBLICATIONS

Charlet, M. et al. (1996) Innate immunity. Isolation of several cysteine-rich antimicrobial peptides from the blood of a mollusc, *Mytilus edulis*. J. Biol. Chem. vol. 271, pp. 21808–21813.*
Chung et al. (1996) Abstracts of the General Meeting of the American Society for Microbiology 96:275.
Hoffmann et al. (1992) Immunology Today 13:411.
Lamberty et al. (1999) Journal of Biological Chemistry 274:9320.

* cited by examiner

*Primary Examiner*—Karen Cochrane Carlson
*Assistant Examiner*—Samuel Wei Liu
(74) *Attorney, Agent, or Firm*—Baker Botts LLP

(57) ABSTRACT

The invention concerns heliomicine, A DNA sequence coding for heliomicine, a vector containing it for transfroming a host organism and the transformation method. The invention concerns heliomicine as a medicine in particular for treating fungal infections. More particularly, it concerns the transformation of plant cells and plants, the heliomicine produced by the transformed plants ensuring their resistance to diseases, in particular diseases of fungal origin.

22 Claims, 2 Drawing Sheets

GENE CODING FOR HELIOMICINE AND USE THEREOF

BACKGROUND OF THE INVENTION

The subject of the present invention is a new cysteine-rich peptide called heliomicine, its use as a medicament and the compositions containing it, a DNA sequence encoding this peptide, a vector containing it for the transformation of a host organism and the method of transforming the said organism.

The invention relates more particularly to the transformation of plant cells and of plants, the heliomicine produced by the transformed plants conferring on them resistance to diseases, in particular of fungal origin.

There is currently an increasing need to make plants resistant to diseases, in particular fungal diseases, in order to reduce or even avoid having to use treatments with antifungal protection products, in order to protect the environment. One means of increasing this resistance to diseases consists in transforming plants so that they produce substances capable of providing their defense against these diseases.

In the field of human health, opportunistic fungal infections exist for which no truly effective treatment currently exists. In particular, this is the case for certain serious invasive mycoses which affect hospital patients whose immune system is suppressed following a transplant, a chemotherapy or human immunodeficiency virus (HIV) infection. Compared with the antimicrobial agent arsenal, the current range of antifungal agents is very limited. A real need therefore exists to characterize and develop new classes of antifungal substances.

Various substances of natural origin, in particular peptides, are known which exhibit bactericidal or fungicidal properties, in particular against the fungi responsible for plant diseases. However, a first problem consists in finding such substances which not only can be produced by transformed plants, but which can still preserve their bactericidal or fungicidal properties and confer them on the said plants. For the purposes of the present invention, bactericidal or fungicidal is understood to mean both the actual bactericidal or fungicidal properties and the bacteriostatic or fungistatic properties.

Cysteine-rich peptides are also known which exhibit bactericidal or bacteriostatic activities, but which do not exhibit fungicidal or fungistatic activity. Another problem consists in finding a cysteine-rich peptide which exhibits a high fungicidal or fungistatic activity compared with the peptides of the state of the art.

Heliomicine is a peptide isolated from the haemolymph of the lepidopteron *Heliothis virescens* which exhibits fungicidal activity against the fungi responsible for plant diseases and the fungi of human or animal pathology. After having first synthesized the gene for heliomicine, it was also found that it could be inserted into a host organism, such as a yeast or a plant, so as to express heliomicine and either produce purified or nonpurified heliomicine, or confer on the said host organism properties of resistance to fungal diseases, providing a particularly advantageous solution to the problems set out above.

Figure 1:
FIG. 1: show a polynucleotide consistion of six oligonucleotides (1–6) which encodes a polypeptide of 44 amino acids of heliomicine.

The subject of the invention is therefore first heliomicine, its use as a medicament or in agrochemistry for the protection of plants, the compositions comprising it, a nucleic acid fragment encoding heliomicine, a chimeric gene comprising the said fragment encoding heliomicine as well as heterologous regulatory elements at the 5' and 3' positions which can function in a host organism, in particular in yeasts or plants and a vector for transforming the host organisms containing this chimeric gene, and the transformed host organism. It also relates to a transformed plant cell containing at least one nucleic acid fragment encoding heliomicine and a plant resistant to diseases containing the said cell, in particular which is regenerated from this cell. It finally relates to a method of transforming plants to make them resistant to diseases into which a gene encoding heliomicine is inserted by means of an appropriate vector. It finally relates to a method of preparing heliomicine by transformed host organisms. p Heliomicine is understood to mean according to the invention any peptide comprising essentially the peptide sequence of formula (I) below,

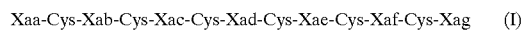

Xaa-Cys-Xab-Cys-Xac-Cys-Xad-Cys-Xae-Cys-Xaf-Cys-Xag     (I)

in which:
Xaa is —NH$_2$ or a peptide residue comprising from 1 to 10 amino acids, preferably from 1 to 6 amino acids,
Xab is a peptide residue comprising from 1 to 1510 amino acids, preferably 10,
Xac is a peptide residue of 3 amino acids,
Xad is a peptide residue comprising from 1 to 9 amino acids, preferably 9,
Xae is a peptide residue comprising from 1 to 7 amino acids, preferably 7,
Xaf is a peptide residue of 1 amino acid, and
Xag is —OH or a peptide residue comprising from 1 to 5 amino acids, preferably 1 or 2 amino acids.

According to a preferred embodiment of the invention, Xaa comprises at least one basic amino acid, and/or Xad comprises at least one basic amino acid. Advantageously, Xad comprises I, 2, 3 or 4 basic amino acids.

Advantageously, Xad represents the following peptide sequence -Lys-Xad'-Xad"-Gly-His-, in which Xad represents a peptide residue of 1 basic amino acid and Xad"

represents a peptide residue comprising from a to 5 amino acids, preferably 5.

Basic amino acids are understood to mean more particularly according to the invention the amino acids chosen from lysine, arginine or homoarginine.

Preferably, Xad represents the folowing peptide sequence -Lys-Arg-Arg-Gly-Tyr-Lys-Gly-Gly-His- (SEQ ID NO:41) or Leu-Leu-Arg-Gly-Tyr-Lys-Gly-Gly-His- (SEQ ID NO49).

According to another preferred embodiment of the invention, Xac comprises at least one acidic amino acid, preferably one.

Advantageously, Xac represents the following peptide sequence -Asn-Xac'-Xac"-, in which Xac represents a peptide residue of 1 amino acid, and Xac represents a peptide residue of 1 acidic amino acid.

Acidic amino acid is understood to mean according to the invention any amino acid comprising on a side chain an organic acid function, more particularly a carboxylic acid preferably chosen from glutamic acid (Glu) or aspartic acid (Asp).

Preferably, Xac represents the following peptide sequence -Asn-Gly-Glu- (SEQ ID NO:50) or Ala-Ala-Glu- (SEQ ID NO:51).

Advantageously, Xaa represents the following peptide sequence Xaa'-Gly-Xaa"- in which Xaa' represents NH2 or a peptide residue comprising 1 to 9 amino acids, preferably 1 to 5 amino acids, and Xaa" represents a peptide residue comprising at least one amino acid, preferably chosen from Leu, Ile, Val, Pro, Ser or Thr, and/or Xab represents the following peptide sequence -Val-Xab'-Asp-, in which Xab' represents a peptide residue comprising from 0 to 8 amino acids, preferably 8, and/or Xae represents the following peptide sequence-Gly-Xae'-Asn-, in which Xae' represents a peptide residue comprising from 0 to 5 amino acids, preferably, and/or Xaf represents one of the following amino acids -Trp-, Phe, Leu, Ile or Val and/or Xag represents the following peptide sequence -Glu-Xag' in which Xag' represents OH or a variable residue having a sequence comprising from 1 to 4 amino acids, preferably 1 amino acid.

According to a more preferred embodiment of the invention, Xaa represents the following peptide sequence NH$_2$-Asp-Lys-Leu-Ile-Gly-Ser- (SEQ ID NO:46) or NH2-Ala-Ala-Ala-Ala-Gly-Ser-, (seq ID NO:52) and/or Xab represents the following peptide sequence -Val-Trp-Gly-Ala-Val-Asn-Tyr-Thr-Ser-Asp- (SEQ ID NO:47), and/or Xae represents the following peptide sequence -Gly-Ser-Phe-Ala-Asn-Val-Asn- (SEQ ID NO:48), and/or Xaf represents the following amino acid -Trp- and/or Xag represents the following peptide sequence -Glu-Thr-OH or -Arg-Thr-OH.

According to a more preferred embodiment of the invention, the heliomicine is the peptidc represented with its coding sequence by the sequence identifier No. 2 (SEQ ID NO:2). The same sequence is described, corresponding to amino acids 6 to 49 of the sequence identifier No. 1 (SEQ ID NO:1) with a different coding sequence.

The NH$_2$-terminal residue may exhibit a post-translational modification, for example an acetylation, likewise the C-terminal residue may exhibit a post-translational modification, for example an amidation.

Peptide sequence comprising essentially the peptide sequence of general formula (I) is understood to mean not only the sequences defined above, but also such sequences comprising at either of their ends, or at both ends, peptide residues necessary for their expression and targeting in a host organism. Host organism is understood to mean any organism comprising at least one cell, whether microorganisms, in particular a yeast or a bacterium, or alternatively plant cells or alternatively higher organisms such as plants.

This may be in particular a "peptide-heliomicine" fusion peptide whose cleavage by the enzymatic systems of the host organism allows there lease of heliomicine, heliomicine being defined above. The peptide fused with heliomicine may be a signal peptide or a transit peptide which makes it possible to control and orient the production of heliomicine in a specific manner in a portion of the host organism, such as for example the cytoplasm, the cell membrane, or in the case of plants in a particular type of cell compartment or of tissues or in the extracellular matrix.

According to one embodiment, the transit peptide may be a signal for chloroplast or mitochondrial homing, which is then cleaved in the chloroplasts or the mitochondria.

According to another embodiment of the invention, the signal peptide may be an N-terminal signal or "prepeptide", optionally in combination with a signal responsible for retaining the protein in the endoplasmic reticulum, or a peptide for vacuolar homing or "propeptide". The endoplasmic reticulum is the site where the operations for processing the protein produced, such as for example the cleavage of the signal peptide, are performed by the "cellular machinery".

The transit peptides may be either single, or double, and in this case optionally separated by an intermediate sequence, that is to say comprising, in the direction of transcription, a sequence encoding a transit peptide of a plant gene encoding a plastid localization enzyme, a portion of sequence of the N-terminal mature part of a plant gene encoding a plastid localization enzyme, and then a sequence encoding a second transit peptide of a plant gene encoding a plastid localization enzyme, as described in application EP 0 508 909.

As transit peptide useful according to the invention, there may be mentioned in particular the signal peptide of the tobacco pahtogen-related protein 1α (PR-1α) gene described by Cornelissen et al., represented with its coding sequence by the sequence identifier No. 2 (SEQ ID NO:2), in particular when heliomicine is produced by plant cells or plants, or the precursor of factor Mat α1 when heliomicine is produced in yeasts.

The fusion peptide "MFα1/heliomicine" with the five residues of the propeptide of factor MFα1(Ser-Leu-Asp-Lys-Arg) (SEQ ID NO:53), which are situated at the N-terminal position, and its coding sequence are part the present invention, described in particular by the sequence identifier No. 1 (SEQ ID NO:1), corresponding to amino acids 1 to 49.

The "PR-1α signal peptide-heliomicine" fusion peptide and its coding sequence are also part of the present invention, described in particular by the sequence identifier No. 3 (SEQ ID NO:3).

The fusion peptide comprising the signal peptide of the maize polygalacturonase PG1. gene fused with heliomicine "PG1 signal peptide/heliomicine" is represented with its coding sequence by the sequence identifiers Nos. 18 and 20 (SEQ ID NO:18 and SEQ ID NO:20).

According to a preferred embodiment of the invention, the cysteine residues of the peptide of formula (I) form at least one intramolecular disulphide bridge, preferably three disulphide bridges. According to a preferred embodiment of the invention, the disulphide bridges are established between the cysteine residues 1 and 4, 2 and 5, and 3 and 6.

Heliomicine is a peptide which is particularly active against fungi and yeasts, and may as such be used preventatively or curatively to protect various organisms against fungal attacks. The present invention therefore relates to heliomicine as a medicament. It also relates to the use of heliomicine for the treatment of plants against fungal attacks, by applying heliomicine directly to the said plants.

The present invention also relates to a composition comprising heliomicine and an appropriate vehicle. The first quality of the appropriate vehicle is not to substantially degrade the heliomicine in the composition, and not to reduce the bactericidal and fungicidal properties of the heliomicine. This composition may be a cosmetic composition and in this case the appropriate vehicle is cosmetically acceptable(suitable in addition for application to the skin or the exoskeleton), or a pharmaceutical composition for a therapeutic use and in this case the appropriate vehicle is pharmaceutically acceptable, appropriate for administration of heliomicine by the topical route per os or by injection, or alternatively an agrochemical composition and in this case the appropriate vehicle is agrochemically acceptable, appropriate for application to plants or in the vicinity of plants, without damaging them.

The present invention also relates to a nucleic acid fragment, in particular DNA, natural or synthetic, encoding the heliomicine defined above, including the "peptide-heliomicine" fusion peptide defined above. It may be according to the invention a fragment which is synthesized or which is isolated from the lepidepteron Heliothis, or alternatively a derived fragment, suitable for the expression of heliomicine in the host organism where the peptide will be expressed. The nucleic acid fragment may be obtained according to standard isolation and purification methods, or alternatively by synthesis according to the customary methods of successive hybridizations of synthetic oligonucleotides. These techniques are in particular described by Ausubel et al.

According to the present invention, "nucleic acid fragment" is understood to mean a nucleotide sequence which may be of the DNA or RNA type, preferably of the DNA type, in particular double-stranded.

According to one embodiment of the invention, the nucleic acid fragment encoding heliomicine comprises the DNA sequence described by bases 16 to 147 of the sequence identifier No. 1 (SEQ ID NO:1), or by the sequence identifier No. 2 (SEQ ID NO:2), in particular the coding portion of this sequence corresponding to bases 1 to 132, a homologous sequence or a sequence complementary to the said sequence.

According to another embodiment of the invention, the nucleic acid fragment encoding the "peptide-heliomicine" fusion peptide comprises the DNA sequence described by the sequence identifier No. 1 (SEQ ID NO:1) or that described by the sequence identifier No. 3 (SEQ ID NO:3), in particular the coding portion corresponding to bases 3 to 224, or that described by the sequence identifier No. 18 (SEQ ID NO:18), in particular the coding portion corresponding to bases 7 to 205, a homologous sequence or a sequence complementary to the said sequences.

"Homologue" is understood to mean according to the invention a nucleic acid fragment exhibiting one or more sequence modifications relative to the nucleotide sequence described by the sequence identifiers Nos. 1, 2 or 3 (SEQ ID NOS:1, 2 or 3) and encoding heliomicine or the "peptide-heliomicine" fusion peptide. These modifications may be obtained according to the customary mutation techniques, or alternatively by choosing the synthetic oligonucleotides used in the preparation of the said sequence by hybridization. In the light of the multiple combinations of nucleic acids which may lead to the expression of the same amino acid, the differences between the reference sequence described by the sequence identifiers Nos. 1, 2 or 3 (SEQ ID NOS:1, 2 or 3) and the corresponding homologue may be substantial, all the more so since small-sized DNA fragments arc involved which can be produced by chemical synthesis. Advantageously, the degree of homology will be at least 70% compared with the reference sequence, preferably at least 80%, more preferably at least 90%. These modifications. are generally neutral, that is to say that they do not affect the primary sequence of the resulting heliomicine or fusion peptide.

The present invention also relates to a chimeric gene (or expression cassette) comprising a coding sequence as well as heterologous regulatory elements at the 5' and 3' positions capable of functioning in a host organism, in particular plant cells or plants, the coding sequence comprising at least one DNA fragment encoding heliomicine or the "peptide-heliomicine" fusion peptide as defined above.

Host organism is understood to mean any lower or higher, mono- or pluricellular organism into which the chimeric gene according to the invention may be introduced, for the production of heliomicine. It includes in particular bacteria, for example *E. coli*, yeasts, in particular of the genera *Saccharomyces* or *Kluyveromyces, Pichia,* fungi, in particular *Aspergillus*, a baculovirus, or preferably plant cells and plants.

"Plant cell" is understood to mean according to the invention any cell derived from a plant and capable of constituting undifferentiated tissues such as calli, differentiated tissues such as embryos, plant portions, plants or seeds.

"Plant" is understood to mean according to the invention any differentiated multicellular organism capable of photosynthesis, in particular monocotyledonous or dicotyledonous plants, more particularly crop plants intended or otherwise as animal or human food, such as maize, wheat, rape, soyabean, rice, sugarcane, beet, tobacco, cotton and the like.

The regulatory elements necessary for the expression of the DNA fragment encoding heliomicine are well known to persons skilled in the art according to the host organism. They comprise in particular promoter sequences, transcription activators, terminator sequences, including start and stop codons. The means and methods for identifying and selecting the regulatory elements are well known to persons skilled in the art.

For the transformation of microorganisms such as yeasts or bacteria, the regulatory elements are well known to persons skilled in the art, and comprise in particular promoter sequences, transcription activators, transit peptides, terminator sequences and start and stop codons.

To direct the expression and the secretion of the peptide in the yeast culture medium, a DNA fragment encoding heliomicine is integrated into a shuttle vector which comprises the following elements:

markers which make it possible to select the transformants. Preferably, the ura-3 gene is used for yeast and the gene which confers resistance to ampicilline for *E. coli,* a nucleic sequence allowing the replication (replication origin) of the plasmid in yeast. Preferably, the replication origin of the yeast 2i plasmid is used, a nucleic sequence allowing the replication (replication origin) of the plasmid in *E. coli,* an expression cassette consisting (1) of a promoter regulatory sequence. Any promoter sequence of a gene which is naturally expressed in yeast may be used. Preferably, the promoter of the *S. cerevisiae* Mfα1 gene is used.

(2) of a sequence encoding a signal peptide (or prepeptide) in combination with a homing peptide (or propeptide). These regions are important for the correct secretion of the peptide. Preferably, the sequence encoding the pre-pro-peptide of the precursor of factor Mfα1 is used.

(3) of a polyadenylation or terminator regulatory sequence. Preferably, the terminator of *S. cerevisiae* phosphoglycerate kinase (PGK) is used. In the expression cassette, the sequence encoding heliomicine is inserted downstream of the pre-pro-sequence and upstream of the PGK terminator.

These elements have been described in several publications including Reichhart et al., 1992, Invert. Reprod. Dev., 21, pp 15–24 and Michaut et al., 1996, FEBS Letters, 395, pp 6–10.

Preferably, yeasts of the *S. cerevisiae* species are transformed with the expression plasmid by the lithium acetate method (Ito et al., 1993, J. Bacteriol, 153, pp 163–168). The transformed yeasts are selected on a selective agar medium which does not contain uracil. The mass production of transformed yeasts is carried out by culturing for 24 h to 48 h in a selective liquid medium.

The transformation of microorganisms makes it possible to produce heliomicine on a larger scale. The present invention therefore also relates to a method of preparing heliomicine, comprising the steps of culturing a transformed microorganism comprising a gene encoding heliomicine as defined above in an appropriate culture medium, followed by the extraction and total or partial purification of the heliomicine obtained.

Preferably, during the extraction of the heliomicine produced by yeasts, the yeasts are removed by centrifugation and the culture supernatant is placed in contact with an acidic solution which may be a solution of an inorganic or organic acid, such as for example hydrochloric acid or acetic acid. The extract obtained is then centrifuged at cold temperature at a speed of 4000 to 10,000 rpm at 4° C. for 30 to 60 min.

The purification of heliomicine may be preceded by a step of fractionation of the supernatant obtained following the extraction step. Preferably, during the fractionation step, the extract is deposited on the reversed phase in order to carry out a solid phase extraction. The washing of the molecules which are soluble in water is carried out with a dilute acidic solution and the elution of the hydrophobic molecules with an appropriate eluant. Good results are obtained with trifluoroacetic acid for the washing and an eluant containing increasing quantities of acetonitrile in dilute acidic solution.

Preferably, the purification of heliomicine is carried out in two stages: a cation-exchange hihg-performance liquid chromatography (HPLC) followed by a reversed phase HPLC with a suitable eluant which may be different from or identical to that of the preceding phase. The various steps of the purification are monitored by a test of inhibition of fungal growth in liquid medium. Preferably, the test is carried out with the fungus *Neurospora crassa*.

The sequence of the heliomicine produced by the transformed yeasts is analyzed according to the method of sequencing by Edman degradation and by mass spectrometry. The structural characterization is carried out directly on the peptide produced, on the peptide modified by reduction/alkylation as well as on fragments of the peptide. The peptide sequence and the molecular mass of the heliomicine produced were compared with those of the native heliomicine extracted from the haemolymph of *H. virescens*. The results show that the two molecules have the same primary structure. The determination of the position of the disulphide bridges indicates that the arrangement of the disulphide bridges is identical in both peptides, the native peptide and the one produced by the transformed microorganism.

The invention relates more particularly to the transformation of plants. As promoter regulatory sequence in plants, it is possible to use any promoter sequence of a gene which is naturally expressed in plants, in particular a promoter of bacterial, viral or plant origin such as, for example, that of a gene for the small subunit of ribulose-biscarboxylase/oxygenase (RuBisCO) or of a plant virus gene such as, for example, that of the cauliflower mosaic (19S or 35S CAMV), or a promoter which is inducible by pathogens such as the tobacco PR-1α, it being possible to use any known suitable promoter. Preferably, a promoter regulatory sequence is used which promotes the overexpression of the coding sequence constitutively or induced by attack by a pathogen, such as for example that comprising at least one histone promoter as described in application EP 0,507,698.

According to the invention, it is also possible to use, in combination with the promoter regulatory sequence, other regulatory sequences which are situated between the promoter and the coding sequence, such as transcription activators (enhancer), such as for example the translation activator of the tobacco mosaic virus (MTV) which is described in application WO 87/07644, or of the tobacco etch virus (TEE) which is described by Carrington & Freed.

As polyadenylation or terminator regulatory sequence, there may be used any corresponding sequence of bacterial origin, such as for example the *Agrobacterium tumefaciens* nos terminator, or alternatively of plant origin, such as for example a histone terminator as described in application EP 0,633,317.

According to the present invention, the chimeric gene may also be combined with a selectable marker suitable for the transformed host organism. Such selectable markers are well known to persons skilled in the art. They may include a gene for resistance to antibiotics, or alternatively a gene for tolerance to herbicides for plants.

The present invention also relates to a cloning or expression vector for the transformation of a host organism containing at least one chimeric gene as defined above. This vector comprises, in addition to the above chimeric gene, at least one replication origin. This vector may consist of a plasmid, a cosmid, a bacteriophage or a virus, which are transformed by the introduction of the chimeric gene according to the invention. Such transformation vectors, according to the host organism to be transformed, are well known to persons skilled in the art and are widely described in the literature.

For the transformation of plant cells or of plants, they may include in particular a virus which may be used for the transformation of developed plants and which contains in addition its own elements for replication and expression. Preferably, the vector for transforming plant cells or plants according to the invention is a plasmid.

The subject of the invention is also a method of transforming host organisms, in particular plant cells by integration of at least one nucleic acid fragment or a chimeric gene as defined above, which transformation may be obtained by any appropriate known means widely described in the specialized literature and in particular the references cited in the present application, more particularly using the vector according to the invention.

A series of methods consists in bombarding cells, protoplasts or tissues with particles to which DNA sequences are attached. Another series of methods consists in using, as means of transfer into plants, a chimeric gene inserted into an *Agrobacterium tumefaciens* Ti or *Agrobacterium rhizogenes* Ri plasmid.

Other methods may be used, such as microinjection or electroporation, or alternatively direct precipitation by means of PEG.

Persons skilled in the art will make the choice of the appropriate method according to the nature of the host organism, in particular of the plant cell or of the plant.

The subject of the present invention is also the host organisms, in particular plant cells or plants, transformed and containing an effective quantity of a chimeric gene comprising a coding sequence for heliomicine defined above.

The subject of the present invention is also the plants containing transformed cells, in particular the plants regenerated from the transformed cells. There generation is obtained by any appropriate means which depends on the nature of the species, as described for example in the above references.

For the methods of transforming plant cells and of regenerating plants, there may be mentioned in particular the following patents and patent applications: U.S. Pat. Nos. 4,459,355, 4,536,475, 5,464,763, 5,177,010, 5,187,073, EP 267,159, EP 604,662, EP 672,752, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442,174, EP 486,233, EP 486,234, EP 539,563, EP 20674,725, WO 91/02701 and WO 95/06128.

The present invention also relates to the transformed plants derived from the cultivation and/or crossing of the above regenerated plants, as well as the seeds of transformed plants.

The plants thus transformed are resistant to certain diseases, in particular to certain fungal or bacterial diseases. As a result, the DNA sequence encoding heliomicine may be integrated with the main objective of producing plants resistant to the said diseases, heliomicine being effective against fungal diseases such as those caused by *Cercospora*, in particular *Cercospora beticola*, *Cladosporium*, in particular *Cladosporium herbarum*, *Fusarium*, in particular *Fusarium culmorum* or *Fusarium graminearum*, or by *Phytophthora*, in particular *Phytophihora cinnamomi*.

The chimeric gene may also comprise, and advantageously, at least one selectable marker, such as one or more genes for tolerance to herbicides.

The DNA sequence encoding heliomicine may also be integrated as a selectable marker during the transformation of plants with other sequences encoding other peptides or proteins of interest, such as for example genes for tolerance to herbicides.

Such genes for tolerance to herbicides are well known to persons skilled in the art and are in particular described in patent applications EP 115,673, WO 87/04181, EP 337,899, WO 96/38567 or WO 97/04103.

Of course the transformed cells and plants according to the invention may comprise, in addition to the sequence encoding heliomicine, other heterologous sequences encoding proteins of interest such as other additional peptides which are capable of conferring on the plant resistance to other diseases of bacterial or fungal origin, and/or other sequences encoding proteins for tolerance to herbicides and/or other sequences encoding proteins for resistance to insects, such as the Bt proteins in particular.

The other sequences may be integrated by means of the same vector comprising a chimeric gene, which comprises a first sequence encoding heliomicine and at least one other sequence encoding another peptide or protein of interest.

They may also be integrated by means of another vector comprising at least the said other sequence, according to the customary techniques defined above.

The plants according to the invention may also be obtained by crossing parents, one carrying the gene according to the invention encoding heliomicine, the other carrying a gene encoding at least one other peptide or protein of interest.

Among the sequences encoding other antifungal peptides, there may be mentioned that encoding drosomycin, which is described in patent application FR 2,725,992 and by Fehlbaum et al.(1994), and in unpublished patent application FR 97 09115 filed on 24 Jul. 1997, or that encoding androctonin which is described in patent application FR 2,745,004 and in unpublished patent application FR 97 10362 filed on 20 Aug. 1997.

The present invention finally relates to a method of cultivating transformed plants according to the invention, the method consisting in planting the seeds of the said transformed plants in a plot of a field appropriate for cultivating the said plants, in applying to the said plot of the said field an agrochemical composition, without substantially affecting the said seeds or the said transformed plants, then in harvesting the cultivated plants when they arrive at the desired maturity and optionally in separating the seeds from the harvested plants.

Agrochemical composition is understood to mean according to the invention any agrochemical composition comprising at least one active product having one of the following activities: herbicide, fungicide, bactericide, virucide or insecticide.

According to a preferred embodiment of the method of cultivation according to the invention, the agrochemical composition comprises at least one active product having at least one fungicidal and/or bactericidal activity, more preferably exhibiting an activity which is complementary to that of the heliomicine produced by the transformed plants according to the invention.

Product exhibiting an activity which is complementary to that of heliomicine is understood to mean according to the invention a product exhibiting a complementary activity spectrum, that is to say a product which will be active against attacks by contaminants (fungi, bacteria or viruses) which are not sensitive to heliomicine, or alternatively a product whose activity spectrum covers that of heliomicine, completely or in part, and whose dose for application will be substantially reduced because of the presence of the heliomicine produced by the transformed plant.

The examples below make it possible to illustrate the present invention without however limiting its scope.

EXAMPLE I

Isolation and Characterization of Heliomicine from the Haemolymph Collected from Immunized Larvae of the Lepidopteron *H. virescens*

EXAMPLE I.1

Isolation 1-1 Induction of the Biological Synthesis of an Antifungal Substance in the Haemolymph of *H. virescens*

The 5th stage mature larvae of the lepidepteron *H. virescens* were immunized with the aid of a needle (30 ga) previously stuck into a pellet of Gram-positive (*M. luteus*) and Gram-negative (*E. coli* 1106) bacteria which is prepared from cultures carried out in a Lauria-Bertani medium for 12 hours at 37° C. The animals thus infected were kept individually in tubes containing an agar-based nutrient medium for 24 hours between 20° C. and 23° C. Before collecting the haemolymph, the larvae were cooled on ice.

1-2 Preparation of the Plasma

The haemolymph (about 30 µl per larva) was collected by excision of an abdominal appendage and collected in 1.5-ml polypropylene microcentrifuge tubes cooled on ice and containing aprotinin as protease inhibitor (20 µg/ml final concentration) and phenylthiourea as melanization inhibitor (final concentration of 20 µl). The haemolymph (2 ml) thus collected from the immunized larvae was centrifuged at 14,000 g for 1 min at 4° C. in order to remove the haemocytes. The haemolymph, free of blood cells, was stored at −20° C. up to its use.

1-3 Acidification of the Plasma

After rapid thawing, the H. virescens plasma was acidified to pH 3 with a 1% trifluoroacetic acid solution. The extraction, under acidic conditions, of the peptide was carried out for 30 min, with gentle stirring, on an ice-cold bath. The extract obtained was then centrifuged at 4° C. for 30 min at 10,000 g.

1-4 Purification of the Peptides a) Prepurification by Solid Phase Extraction

A quantity of extract equivalent to 2 ml of haemolymph was deposited on a reversed-phase support, as marketed in the form of a cartridge (Sep-Pak™ C18, Waters Associates), equilibrated with acidified water (0.05% TFA). The hydrophilic molecules were removed by a simple wash with acidified water. The elution of the peptide was carried out with a 40% acetonitrile solution prepared in 0.05% TFA. The fraction eluted at 40% of acetonitrile was dried under vacuum with the aim of removing the acetonitrile and the TFA and then it was reconstituted in sterile ultrapure water before being subjected to the first purification step.

b) Purification by High-performance Liquid Chromatography (HPLC) on a Reversed-phase Column

- first step: the fraction containing the peptide was analyzed by reversed-phase chromatography on an Aquapore RP-300 $C_8$ semipreparative column (Brownlee™, 220×70 mm, 300 Å), the elution was carried out using a linear gradient of acetonitrile from 2 to 60% in 0.05% TFA over 120 minutes at a constant flow rate of 1.5 ml/min. The fractions were collected manually, monitoring the variation of the absorbance at 225 nm and 254 nm. The fractions collected were dried under vacuum, reconstituted with ultrapure water and analyzed for their antifungal activity using the test described below.

- second step: the antifungal fraction corresponding to the peptide was analyzed on an Aquapore RP-300 $C_8$ reversed-phase analytical column (Brownlee™, 220×4.6 mm, 300 Å), using a biphasic linear gradient of acetonitrile from 2% to 22% over 10 min and from 22 to 32% over 50 min in 0.05% TFA with a constant flow rate of 0.8 ml/min. The fractions were collected manually, monitoring the variation of the absorbance at 225 nm and 254 nm. The fractions collected were dried under vacuum, reconstituted with ultrapure water and analyzed for their antifungal activity under the conditions described below.

- third step: the antifungal fraction containing the peptide was purified to homogeneity on a Narrowbore Delta-Pak™ HPI $C_{18}$ reversed-phase column (Waters Associates, 150× 2.2 mm) using a biphasic linear gradient of acetonitrile from 2% to 24% over 10 min and from 24 to 44% over 100 min in 0.05% TFA with a constant flow rate of 0.25 ml/min at a controlled temperature of 30° C. The fractions were collected manually, monitoring the variation of the absorbance at 225 nm. The fractions collected were dried under vacuum, reconstituted with filtered ultrapure water and analyzed for their antifungal activity.

EXAMPLE I1.2

Structural Characterization of the Peptide 2-1 Verification of Purity by Zonal Capillary Electrophoresis The purity of the antifungal peptide was verified by zonal capillary electrophoresis on a 270-HT model(PEApplied Biosystems division of Perkin Elmer). 1 nl of a 50 µM solution of purified peptide was injected with the aid of a vacuum into a silica capillary (72 cm×50 µm) and the analysis was carried out in a 20 mM citrate buffer at pH 2.5. The electrophoresis was carried out at 20 kV from the anode to the cathode for 20 min at 30° C. The migration was recorded at 200 nm.

2-2 Determination of the Number of Cysteines: Reduction and S-pyridylethylation.

The number of cysteine residues was determined on the native peptide by reduction and S-pyridylethylation. 100 pmol of native peptide were reduced in 40 µl of 0.5 M Tris-HCl buffer, pH 7.5 containing 2 mM EDTA and 6 M guanidinium chloride in the presence of 2 µl of 2.2 M dithiothreitol. The reaction medium was placed under a nitrogen atmosphere. After incubating for 60 min in the dark, 2 µl of freshly distilled 4-vinylpyridine were added to the reaction which was then incubated for 10 min at 45° C. in the dark and under a nitrogen atmosphere. The pyridylethylated peptide was then separated from the constituents of the reaction medium by reversed-phase chromatography using a linear gradient of acetonitrile in the presence of 0.05% TFA.

2-3 Determination of the Mass of the Native Peptide, of the S-pyridylethylated Peptide and of the Proteolysis Fragments by MALDI-TOF (Matrix Assisted Laser Desorption Ionization-Time of Flight) Mass Spectrometry The mass measurements were carried out on a Bruker Biflex MALDI-TOF mass spectrometer (Bremen, Germany) in a positive linear mode. The mass spectra were calibrated externally with a standard mixture of peptides of known m/z, respectively 2199.5 Da, 3046.4 Da and 4890.5 Da. The various products to be analyzed were deposited on a thin layer of α-cyano-4-hydroxycinnamic acid crystals which is obtained by rapid evaporation of a solution saturated with ethanol. After drying under a moderate vacuum, the samples were washed with a drop of 0.1% trifluoroacetic acid before being introduced into the mass spectrum.

2-4 Sequencing by Edman Degradation

The automated sequencing by Edman degradation of the native peptide, of the S-pyridylethylated peptide and of the various fragments obtained after the various proteolytic cleavages and the detection of the phenylthiohydantoin derivatives were carried out on an ABI473A sequencer (PEApplied Biosystems division of Perkin Elmer).

2-5 Proteolytic Cleavages

- Confirmation of the Peptide Sequence in the C-terminal Region 200 pmol of reduced and S-pyridylethylated peptide were incubated in the presence of 5 pmol of endoproteinase-Lys-C (Acromobacter protease I, specific cleavage of the lysine residues on the C-terminal side, Takara, Otsu) according to the conditions recommended by the supplier (10 mM Tris-HCl, pH 9, in the presence of 0.01% Tween 20). After stopping the reaction with 1% TFA, the peptide fragments were separated by reversed-phase HPLC on a Narrowbore Delta-Pak™ HPI $C_{18}$ type column(Waters Associates 150×2 mm) in a linear gradient of acetonitrile from 2 to 60% over 80 min in 0.05% TFA with a flow rate of 0.2 ml/min and a constant temperature of 37° C. The fragments obtained were analyzed by MALDI-TOF mass spectrometry and the peptide corresponding to the C-terminal fragment was sequenced by Edman degradation.

- Determination of the Arrangement of the Disulphide Bridges by Proteolysis with Thermolysin The native peptide (8 μg) was incubated for 1 hour in the presence of 4 μg of thermolysin (Boehringer Mannheim, thermolysin/peptide ratio, ½ by weight: weight) at 37° C. in 0.1 M MES (N-ethylmorpholine) buffer at pH 7 in the presence of 2 mM $CaCl_2$. The reaction was stopped by addition of formic acid and the reaction products were immediately separated by reversed-phase chromatography on a Narrowbore Delta-Pak™ HPI $C_{18}$ column (Waters Associates, 150×2.2 mm) in a linear gradient of acetonitrile from 2 to 50% over 100 min in 0.05% TFA at the flow rate of 0.2 ml/min at 30° C. preceded by an isocratic step at 2% acetonitrile over 10 min. The fragments obtained were analyzed by MALDI-TOF mass spectrometry and sequenced by Edman degradation.

EXAMPLE II

Expression of Heliomicine in the Yeast *Saccharomyces cerevisiae*

All the techniques used below are standard laboratory techniques. The detailed protocols for these techniques have been described in particular in Ausubel et al.

EXAMPLE I-1I

Assembling of the Synthetic Gene

Assembling was carried out using 6 synthetic oligonucleotides encoding the 44 amino acids of heliomicine preceded by the 5 C-terminal amino acids of the pre-pro sequence of factor α1 (Mfα1) of the yeast. The oligonucleotides represented in FIG. 1 were chosen taking into account the preferential codons used by *S. cerevisiae*.

The assembling took place in several steps:
oligonucleotides 2 to 5 were phosphorylated at their 5' ends by the action of polynucleotide kinase (New England Biolabs);
oligonucleotides 1 to 6 were mixed, heated to 100° C. and hybridized by slowly reducing the temperature to 25° C. over 3 hours;
the hybridized oligonucleotides were subjected to a treatment with T4 bacteriophage ligase (New England Biolabs) for 15 hours at 15° C.;
the DNA unit resulting from the hybridization of the oligonucleotides which is represented in FIG. 1, flanked by the HinDIII and BglII restriction sites, was inserted into the plasmid Bluescript SK+ (Stratagene) digested with the enzymes HinDIII and BamHI (BglII and BamHI are compatible). The ligation mixture was then used to transform competent *E. coli* DH5α cells (Stratagene). Several clones were analyzed and sequenced. One of these clones which had the desired sequence was called pSEA1.

EXAMPLE II-2

Construction of the Vector pSEA2 which Allows the Secretion of the Heliomicine Synthesized The HinDIII-SalI DNA fragment of the vector pSEA1, carrying the sequence encoding heliomicine as well as the SphI-HinDIII fragment of the vector M13JM132 (Michaut et al., 1985, FEBS Letters, 395, pp 6–10) were inserted between the SphI and SalI sites of the plasmid pTG4812 (Michaut et al., 1996, FEBS Letters, 395, pp 6–10). The SphI-HinDIII fragment of the vector M13JM132 contains the sequence of the promoter of the MFα1 gene of the yeast as well as the sequence encoding the pre-pro region of factor MFα1. In the resulting plasmid pSEA2, the synthetic gene for heliomicine therefore finds itself inserted between the pre-pro sequences of factor Mfα1 and the transcription terminator; this construct should therefore ensure the maturation and the secretion of heliomicine.

EXAMPLE II-3

Transformation of a Strain of *S. cerevisiae* with the DNA of the Plasmid pSEA2 and Analysis of the Transformants The yeast strain TGY 48.1 (MATa, ura3-D5, his, pra1, prb1, prc1, cps1; Reichhart et al., 1992, Invert. Reprod. Dev. 21, pp 15–24) was transformed with the plasmid pSEA2. The transformants were selected at 29° C. on a selective YNBG medium (0.67% yeast nitrogen base, 2% glucose), supplemented with 0.5% of casamino acids and containing no uracil. After transformation, several yeast clones, selected for the ura+character, were cultured for 48 h at 29° C. in 50 ml of selective medium. After centrifugation (4000 g, 30 min, 4° C.), the supernatant was acidified to pH 3.5 with acetic acid, before being deposited on a Sep-Pak™ $C_{18}$ cartridge (Waters Associates) equilibrated with acidified water (0.05% TFA). The various proteins bound to the cartridge were eluted with solutions of 0.05% TFA containing increasing percentages of acetonitrile.

The 40% fraction, exhibiting an antifungal activity, was analyzed by HPLC on an Aquapore RP-300 $C_8$ reversed-phase analytical column (Brownlee™, 220×4.6 mm, 300 Å), using a linear gradient of acetonitrile from 2% to 40% over 80 min in 0.05% TFA with a constant flow rate of 0.8 ml/min. The fractions were collected manually by monitoring the variation in absorbance at 225 nm and 254 nm. The fractions collected were dried under vacuum, reconstituted with ultra pure water and analyzed for their antifungal activity under the conditions described in Example III. The structural characterization of the peptide was carried out as described in Example 1.2.

EXAMPLE II-4

Production of Recombinant Heliomicine on a Semi-preparative Scale

One of the clones of transformed yeast expressing heliomicine was cultured at 29° C. for 24 h in 5100 ml of selective medium. This procedure was then used to inoculate 4l of selective medium and the culture was carried out for 48 h at 29° C. The yeasts were removed by centrifugation (4000 g, 30 min, 4° C.).The supernatant was acidified to pH 3.5 with acetic acid, subjected to a second centrifugation (4000 g, 30 min, 4° C.) before being deposited on a ClB preparative reversed-phase open column (Waters Associates), 125 Å, 6 g of phase per 500 ml of supernatant) equilibrated with acidified water (0.05% TFA). The hydrophilic molecules were removed by a wash with acidified water followed by a wash with a 15% solution of acetonitrile prepared in 0.05% TFA. The elution of the peptide was carried out using a 40% acetonitrile solution prepared in 0.05% TFA. The fraction eluted at 40% acetonitrile was lyophilized and then reconstituted in sterile ultrapure water before being subjected to the first purification step.

- first step of purification by HPLC: the purified fraction containing heliomicine was reconstituted in a 25 mM ammonium acetate solution, pH 3.4. This sample was injected into an Aquapore Cation Exchange preparative cation-exchange column (Brownlee™ 250×10 mm), using a linear gradient of NaCl from 0% to 100% over 90 min in 25 mM ammonium acetate, pH 3.4 with a constant flow rate of 2 ml/min. The fractions collected were dried under vacuum, reconstituted with ultrapure water and analyzed for their antifungal activity under the conditions described below.

- second step of purification by HPLC: the heliomicine was purified to homogeneity by chromatography on an Aquapore RP-300 $C_8$ semipreparative reversed-phase column (Brownlee™, 220×7 mm, 300 Å), using a linear gradient of acetonitrile from 2% to 40% over 80 min in 0.05% TFA with a constant flow rate of 2 ml/min.

EXAMPLE III

Test of Activity in vitro: Measurement of the Antifungal Activity by Microspectrophotometry This methodology was used to test for the antifungal molecules during the various purification steps, for the determination of the activity spectrum of the peptide and for the determination of the minimum inhibitory concentration (MIC) at which the peptide was active. The MIC was expressed as the concentration range [a]–[b] where [a] was the minimum concentration where the start of growth is observed and [b] the concentration for which no growth was observed. Examples of the specific activity of heliomicine, against filamentous fungi and yeasts, are given in Tables 1 and 2.

EXAMPLE III-1

Test for Detection of Activity Against Filamentous Fungi

The antifungal activity was detected by a test for inhibition of growth in a liquid medium. The spores of the fungi to be tested were suspended in a culture medium of the "potato-glucose" type. Preferably, 12 g of Potato Dextrose Broth medium (Difco) were used per 1 l of demineralized water. Two antibiotics were added to the culture medium: tetracycline (final concentration of 10 μg/ml) and cefotaxime (100 μg/ml). 10 μl of each fraction to be analysed are deposited in microtitre plates in the presence of 90 μl of culture medium containing the spores (at a final concentration of 104 spores/ml). The incubation was carried out in a humid chamber at 30° C. for 48 hours. Fungal growth was observed under a light microscope after 24 h and quantified after 48 hours by measuring the absorbance at 600 nm with the aid of a spectrophotometric microtitre plate reader.

- filamentous fungi tested: *Aspergillus fumigatus* (gift from Dr H. Koenig, Hôpital Civil, Strasbourg); *Nectria haemotococca, Fusarium culmorum, Trichoderma viride* (fungus culture collection of the Universite Catholique of Leuven, Belgium); *Neurospora crassa, Fusarium oxysporum*, (fungus culture collection of Societe Clause, Paris).

The results of the test of heliomicine activity against filamentous fungi are presented in Table 1 below.

TABLE 1

Activity Of Heliomicine Against Filamentous Fungi

| Fungi | MIC of heliomicine (μM) |
|---|---|
| Neurospora crassa | 0.1–0.2 |
| Fusarium culmorum | 0.2–0.4 |
| Fusarium oxysporum | 1.5–3 |
| Nectria haematococca | 0.4–0.8 |
| Trichoderma viride | 1.5–3 |
| Aspergillus fumigatus | 6–12.5 |

EXAMPLE III-2

Test for Detection of Activity Against Yeasts

The various yeast strains were incubated in a "Sabouraud" type culture medium and incubated at 30° C. for 24 h with gentle stirring. The test sample (10 μl) was deposited in microtitre plate wells to which there were added 90 μl of a dilute yeast culture whose density was adjusted to OD 600=0.001. Growth was evaluated by measuring the absorbance at 600 nm with the aid of a spectrophotometric microtitre plate reader.

- yeasts tested: *Candida albicans, C. glabrata, C. tropicalis, C. krusei, C. inconspicua, Cryptococcus neoformans, Cryp. albidus, Saccharomyces cerevisiae* (gift from Dr. H. Koenig, Hôpital civil, Strasbourg).

The results of the test of heliomicine activity against yeasts are presented in Table 2 below.

TABLE 2

Activity Of Heliomicine Against Yeasts

| Yeasts | MIC of heliomicine (μM) |
|---|---|
| Candida albicans | 2.5–5 |
| Candida tropicalis | 2.5–5 |
| Candida krusei | 10–20 |
| Candida inconspicua | 5–10 |
| Cryptococcus neoformans | 2.5–5 |
| Cryptococcus albidus | 5–10 |

These results show the excellent antifungal activity of the peptide according to the invention.

EXAMPLE IV

Preparation of a Transformed Plant Comprising a Gene Encoding Heliomicine

This example describes the preparation of the sequence encoding heliomicine for its expression in a plant cell, of the chimeric gene, of the integrating vector and of the transformed plants. FIGS. 2 to 6 in the annex describe the schematic structures of some plasmids prepared for the construction of the chimeric genes. In these figures, the various restriction sites are marked in italics.

All the techniques used below are standard laboratory techniques. The detailed protocols for these techniques are in particular described in Ausubel et al.

EXAMPLE IV-1

Construction of the Chimeric Genes for the Transformation of Plants pRPA-MD-P: Creation of a Plasmid Containing the Signal Peptide of the Tobacco PR-la Gene The two complementary synthetic oligonucleotides Oligo 7 and Oligo 8 below are hybridized at 65° C. for 5 minutes and by slow reduction of the temperature to 30° C. over 30'.

Oligo 7: 5' GCGTCGACGC GATGGGTTTC GTGCTTTTCT CTCAGCTTCC ATCTTTCCTT CTTGTGTCTA CTCTTCTTCT TTTCC 3' (SEQ ID NO:5)

Oligo 8: 5' TCGCCGGCAC GGCAAGAGTA AGAGAT-CACA AGGAAAAGAA GAAGAGTAGA CACAA-GAAGG AAAGATGGAA GC 3' (SEQ ID NO:6)

After hybridization between Oligo 7 and Oligo 8, the DNA remaining single-stranded serves as template for the Klenow fragment of *E. coli* polymerase I (under the standard conditions recommended by the manufacturer (New England Biolabs)) for the creation of the double-stranded oligonucleotide starting from the 3' end of each oligo. The double-stranded oligonucleotide obtained is then digested with the restriction enzymes SacII and NaeI and cloned into the plasmid pBS II SK(−) (Stratagene) digested with the same restriction enzymes. A clone is then obtained which comprises the region encoding the signal peptide of the tobacco PR-1α gene (SEQ ID NO:4).

pRPA-PS-PR1a-helio: Creation of a Sequence Encoding Heliomicine Fused with the PR-1α Signal Peptide with no Untranscribed Region in 3'

The two synthetic oligonucleotides complementary to Oligo 9 and Oligo 10 sequences according to the operating conditions described for pRPA-MD-P.

Oligo 9: 5' GATAAGCTTA TCGGTTCCTG CGT-GTGGGGT GCTGTGAACT ACACTTCCGA TTG-CAACCGT GAGTGCAAGA GGAGGGGTTA 3' (SEQ ID NO:7)

Oligo 10: 5' CCGGATCCGT CGACACGTTC GCCTCGC-CGA GCTCTCAAGT CTCGCACCAG CAGTTCACGT TAGCGAAGGA ACCGCAGTGA CCACCCTTGT AACCCCTCCT CTTGCACTC 3' (SEQ ID NO:8)

Figure 2:
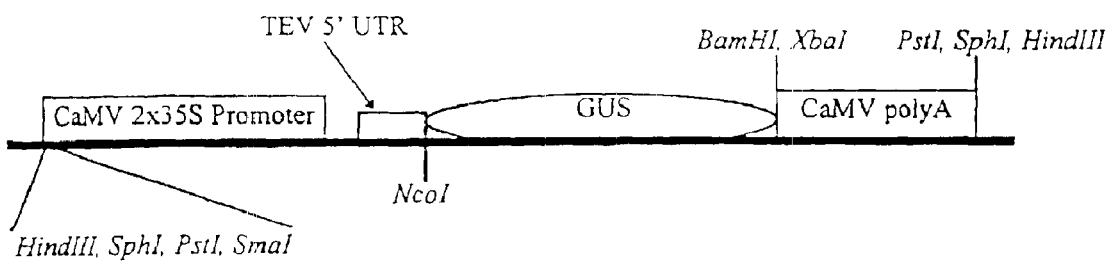
FIG. 2: show a schematic structure of plasmid pRTL-2GUS which comprises duplicated CaMV 35S promoter, tobacco etch virus (TEV) 5' untranslated sequence, *E.coli* β-glucoronidase gene and a CaMV 35S RNA polyadenylation site.

After hybridization between Oligo 9 and Oligo 10, the DNA remaining single-stranded serves as template for the Klenow fragment of *E. coli* polymerase I (under the standard conditions recommended by the manufacturer (New England Biolabs)) for the creation of the double-stranded oligonucleotide starting from the 3' end of each oligo. This double-stranded oligonucleotide containing the coding portion of heliomicine (SEQ ID NO:2) is then cloned directly into the plasmid pRPA-MD-P which has been digested with the restriction enzyme NaeI. The correct orientation of the clone obtained is checked by sequencing. A clone is then obtained which comprises the region encoding the PR-1α-heliomicine fusion protein situated between the NcoI restriction sites at the N-terminal end and the ScaI, SacII and BamHI restriction sites at the C-terminal end (SEQ ID NO:3)

pRPA-RD-239: Creation of a Vector for Expression in Plants Comprising the Sequence Encoding the PR-1α-heliomicine Fusion Protein The plasmid pRTL-2 GUS, derived from the plasmid pUC-19, was obtained from Dr. Jim Carrington (Texas A&M University, not described). This plasmid, whose schematic structure is represented in FIG. 2, contains the duplicated CaMV 35S promoter isolated from the cauliflower mosaic virus (CaMV 2×35S promoter; Odell et al., 1985) which directs the expression of an RNA containing the tobacco etch virus 5' untranslated sequence (TEV 5' UTR; Carrington & Freed, 1990), the *E. coli* β-glucuronidase gene (GUS Jefferson et al., 1987) followed by the CaMV 35S RNA polyadenylation site (CaMV polyA; Odell et al, 1985).

Figure 3:
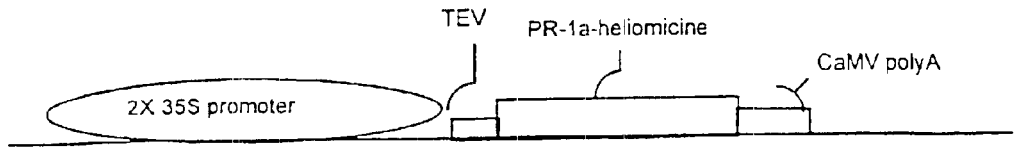
FIG. 3: show a cassette for expressing a PR-1α-heliomicine fusion protein in the pRTL-2GUS plasmid.

The plasmid pRTL-2 GUS is digested with the restriction enzymes NcoI and BamHI and the large DNA fragment is purified. The plasmid pRPA-PS-PR1α-helio is digested with the restriction enzymes NcoI and BamHI and the small DNA fragment containing the region encoding the PR-1α-heliomicine fusion protein is purified. The two purified DNA fragments are then ligated together into a cassette for expression in plants which synthesizes a PR-1α-heliomicine fusion protein. The schematic structure of this expression cassette is represented in FIG. 3. "PR-1α-heliomicine" represents the coding region for the PR-1a -heliomicine fusion protein of pRPA-RD-239. The heliomicine is transported to the extra cellular matrix of the plant by the action of the PR-1a signal peptide pRPA-RD-195: Creation of a Plasmid Containing a Modified Multiple Cloning Site The plasmid pRPA-RD-195 is a plasmid derived from pUC-19 which contains a modified multiple cloning site. The complementary synthetic oligonucleotides Oligo 11 and Oligo 12 below are hybridized and made double-stranded according to the procedure described for pRPA-MD-P.

Oligo 11: 5' AGGGCCCCCT AGGGTTTAAA CGGC-CAGTCA GGCCGAATTC GAGCTCGGTA CCCGGG-GATC CTCTAGAGTC GACCTGCAGG CATGC 3' (SEQ ID NO:9)

Oligo 12: 5' CCCTGAACCA GGCTCGAGGG CGCGC-CTTAA TTAAAAGCTT GCATGCCTGC AGGTC-GACTC TAGAGG 3' (SEQ ID NO:10)

Figure 4:
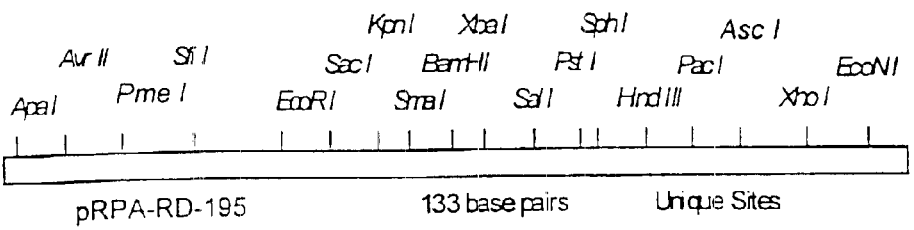
FIG. 4: show a schematic structure of multiple cloning site for facilitating the induction of the cassettes for expression using an *Argrobacterium tumefaciens* vector.

The double-stranded oligonucleotide obtained is then ligated into pUC-19 which has been previously digested with the restriction enzymes EcoRI and HindIII and made blunt-ended using the Klenow fragment of *E. coli* DNA polymerase I. A vector is obtained which contains multiple cloning sites in order to facilitate the introduction of the cassettes for expression in an *Agrobacterium tumefaciens* vector plasmid. The schematic structure of this multiple cloning site is represented in FIG. 4.

pRPA-RD-240: Introduction of the Cassette for Expression of PR-1α-heliomicine from pRPA-RD-239 into pRPA-RD-195

The plasmid pRPA-RD-239 is digested with the restriction enzyme PstII. The DNA fragment containing the cassette for expression of PR-1α-heliomicine is purified. The purified fragment is then ligated into pRPA-RP-195 which has been previously digested with the restriction enzyme PstII and dephosphorylated with calf intestinal phosphatase.

pRPA-RD-174: Plasmid Derived from pRPA-BL-1SOA(EP 0,508,909) Containing the Gene for Tolerance to Bromoxynil of pRPA-BL-237 (EP 0,508,909)

The gene for tolerance to bromoxynil is isolated from pRPA-BL-237 by gene amplification by PCR. The fragment obtained is blunt-ended and is cloned into the EcoRI site of pRPA-BL-150A which has been made blunt-ended by the action of Klenow polymerase under standard conditions. An *Agrobacterium tumefaciens* vector is obtained which contains the gene for tolerance to bromoxynil near its right border, a gene for tolerance to kanamycin near its left border and a multiple cloning site between these two genes.

Figure 5:
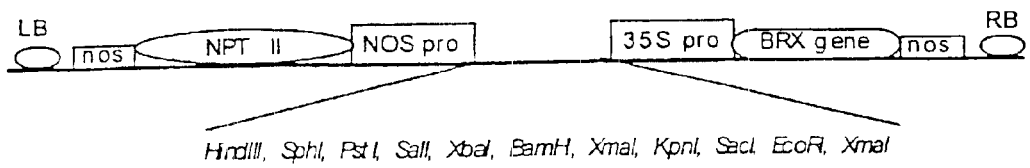
FIG. 5: show a schematic structure of pRPA-RD-174 wherein "nos" represents the *Argrobacterium tumefaciens* nopaline synthase polyadenylation site; "NPT" stands for the *E.coli* Tn5 transposon neomycin phosphotransferase gene; "NPS pro" represents the *Argrobacterium tumefaciens* nopaline synthase promotor; "35S pro" represents the 35S promotor from cauliflower mosaic virus; "BRX" stands for the nitralase gene from *K.ozaenae*; and, "RB" and "LB" represent right and left borders, respectively, of the sequence of an *Argrobacterium tumefaciens* Ti plasmid.

The schematic structure of pRPA-RD-174 is represented in FIG. 5. In this figure, "nos" represents the *Agrobacterium tumefaciens* nopaline synthase polyadenylation site (Bevan et al., 1983), "NOS pro" represents the *Agrobacterium tumefaciens* nopaline synthase promoter (Bevan et al., 1983), "NPTII" represents the *E. coli* Tn5 transposon neomycin phosphotransferase gene (Rothstein et al., 1981), "35S pro" represents the 35S promoter isolated from the cauliflower mosaic virus (Odell et al., 1985), "BRX" represents the nitralase gene isolated from *K. ozaenae* (Stalker et al., 1988), "RB" and "LB" represent the right and left borders respectively of the sequence of an *Agrobacterium tumefaciens* Ti plasmid.

pRPA-RD-184: Addition of a New Unique Restriction Site into pRPA-RD-174

The complementary synthetic oligonucleotides Oligo 13 and Oligo 14 below are hybridized and made blunt-ended according to the procedure described for pRPA-MD-P.

Oligo 13: 5' CCGGCCAGTC AGGCCACACT TAAT-TAAGTT TAAACGCGGC CCCGGCGCGC CTAGGT-GTGT GCTCGAGGGC CCAACCTCAG TACCTG-GTTC AGG 3' (SEQ ID NO:11)

Oligo 14: 5' CCGGCCTGAA CCAGGTACTG AGGT-TGGGCC CTCGAGCACA CACCTAGGCG CGC-CGGGGCC GCGTTTAAAC TTAATTAAGT GTGGC-CTGAC TGG 3' (SEQ ID NO:12)

The hybridized double-stranded oligonucleotide (95 base pairs) is purified after separation on an agarose gel (3% Nusieve, FMC). The plasmid pRPA-RD-174 is digested with the restriction enzyme XmaI, and the large DNA fragment is purified. The two DNA fragments obtained are then ligated.

A plasmid derived from pRPA-RD-174 is obtained which comprises other restriction sites between the gene for tolerance to bromoxynil and the selectable marker kanamycin gene.

Figure 6:
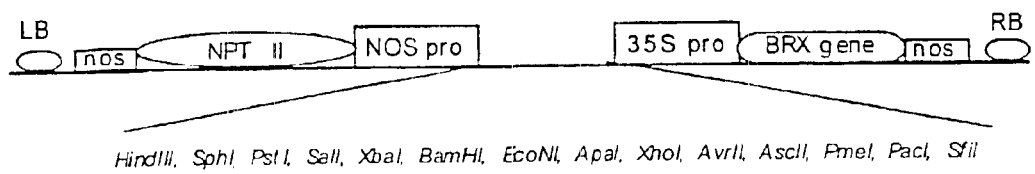
FIG. 6: show a schematic structure of pRPA-RD-184 wherein the terms "nos", "NPT", "NPS pro", "35S pro", "BRX", "RB" and "LB" have the same meaning as in FIG. 5.

The schematic structure of the plasmid pRPA-RD-184 is represented in FIG. 6 where the terms "nos", "NPT-II", "NOS pro", 35S pro", "BRX gene", "RB" and "LB" have the same meaning as in FIG. 5.

pRPA-RD-241: Creation of an *Agrobacterium tumefaciens* Vector Containing the Construct of the Gene Encoding Heliomicine Directed Towards the Extracellular Matrix The plasmid pRPA-RD-240 is digested with the restriction enzymes SfiII and AscI and the DNA fragment containing the PR-1α-heliomicine gene is purified. The plasmid pRPA-RD-184 is digested with the same restriction enzymes. The DNA fragment containing the cassette for expression of PR-1α-heliomicine is then ligated into pRPA-RD-184. An *Agrobacterium tumefaciens* vector is thus obtained which contains the sequence encoding the PR-1α-heliomicine fusion protein which leads to the expression of heliomicine in the extracellular matrix of the plant.

EXAMPLE IV-2

Creation of an Expression Cassette CsVMV Promoter - PG1 Signal Peptide-heliomicine-Nos terminator pRPA-NP4: Creation of a Plasmid Containing the Signal Peptide of the Maize Polygalacturonase PGI Gene(Genbank, Accession No. X57627)

The two partially complementary synthetic oligonucleotides Oligo 13 and Oligo 14 below are hybridized at 65° C. for 5 minutes and then by slowly reducing the temperature to 30° C. over 30 minutes.

Oligo 15: 5' GGTCTAGAAT GGCCTGCACC AACAACGCCA TGAGGGCCCT CTTCCTCCTC 3' (SEQ ID NO:13)

Oligo 16: 5' CCGAATTCGG CGCCGTGCAC GATGCA-GAAG AGCACGAGGA GGAAGAGGGC 3' (SEQ ID NO:14)

After hybridization between Oligo 13 and Oligo 14, the DNA remaining single-stranded serves as template for the Klenow fragment of *E. coli* polymerase I (under the standard conditions recommended by the manufacturer (New England Biolabs)) for the creation of the double-stranded oligonucleotide starting from the 3' end of each oligo. The double-stranded oligonucleotide obtained is then digested with the restriction enzymes XbaI and EcoRI and then cloned into the plasmid pBS II SK(-)(Stratagene) digested with the same restriction enzymes. A clone is then obtained which contains the region encoding the 22 amino acids of the signal peptide of the PG1 gene, and which may be fused with the reading frame of other proteins at the level of the SfoI site (SEQ ID NO:15).

pRPA-NP5: Creation of a Sequence Encoding Heliomicine Fused with the Signal Peptide of the PG1 Gene The region encoding heliomicine was amplified by PCR from the clone pRPA-PS-PR1α-helio (SEQ ID NO:3) with the thermostable Pfu enzyme (Stratagene) according to the standard conditions recommended by the manufacturer. The synthetic oligonucleotides used for this amplification are:

Oligo 17: 5' GATAAGCTTA TCGGTTCCTG CGTG 3' (SEQ ID NO:16)

Oligo 18: 5' GGCTCGAGTC AAGTCTCGCA CCAG-CAGTTC AC 3' (SEQ ID NO:17)

The PCR product was digested with the restriction enzyme XhoI and cloned into the vector pRPA-NP4 digested with the restriction enzymes SfoI and XhoI. The resulting clone therefore comprises the region encoding the signal peptide of the PG1 gene fused in the same reading frame with the sequence encoding heliomicine (SEQ ID NO:18).

pRPA-NP6: Creation of a Cassette for Expression of Heliomicine in a Transformation Vector The expression and transformation vector pILTAB 357 is derived from the binary vector pBin19. It contains the CsVMV promoter (Verdaguer et al. 1996, Plant Mol. Biol. 31, 1129–1139) followed by a multiple cloning site and the nopaline synthase Nos transcription terminator (FIG. X+1). The sequence of this fragment is indicated (SEQ ID NO:19).

The heliomicine expression vector was obtained by insertion of the XbaI-KpnI restriction fragment of the vector pRPA-NP5 containing the PG1 signal peptide-heliomicine fusion into the vector pILTAB 357 digested with these same enzymes. The resulting clone therefore contains the expression cassette CsVMV promoter-PG1 signal peptide-heliomicine-Nos terminator (SEQ ID NO:20).

EXAMPLE IV-3

Preparation of Transformed Tobacco 3.1—Transformation

The vectors pRPA-RD-241 and pRPA-NP6 are introduced into the *Agrobacterium tumefaciens* EHA101 or EHA105 strain (Hood et al., 1987) carrying the cosmid pTVK291 (Komari et al., 1986). The transformation technique is based on the procedure of Horsh et al. (1985).

3.2—Regeneration

The regeneration of the PBD6 tobacco (origin SEITA France) from foliar explants is carried out on a Murashige and Skoog (MS) basic medium comprising 30 g/l of sucrose as well as 200 μg/ml of kanamycin. The foliar explants are collected from plants cultivated in a greenhouse or in vitro and regenerated according to the foliar disc technique (Horsh et al., 1985). in three successive stages: the first comprises the induction of shoots on a medium supplemented with 30 g/l of sucrose containing 0.05 mg/l of naphthylacetic acid (ANA) and 2 mg/l of benzylaminopurine (BAP) for 15 days. The shoots formed during this stage are then developed for 10 days by culturing on an MS medium supplemented with 30 g/l of sucrose but containing no hormone. Next, developed shoots are collected and they are cultivated on an MS rooting medium containing half the content of salt, vitamins and sugar and containing no hormone. After about 15 days, the rooted shoots are transferred into soil.

3.3—Analysis of the Expression of Heliomicine in Transgenic Tobacco a) Production of Specific Polyclonal Antibodies Polyclonal antibodies were obtained by immunizing a rabbit with native heliomicine according to the usual procedures of the Centre de Bioexperimentation VALBEX (IUT A - Lyon I). The serum obtained (15 ml) was then immunopurified on Sepharose 4B column (Pharmacia; ref 17-0430-01) coupled to heliomicine so as to specifically select the immunoglobulins which recognize this peptide. These antibodies were finally eluted in 6 ml of glycine (200 mM; pH 3), neutralized with 1 M Tris pH 9.5, dialysed with 0.5×PBS, and stored frozen at −20° C. up to the time of use.

b) Immunodetection of Heliomicine Intransgenic Tobacco

Analysis of the expression of heliomicine was conducted on 8 transgenic plants for the construct pRPA-NP6, as well as on a wild-type control. Well-developed leaves of tobacco in a greenhouse were finely ground at the temperature of liquid nitrogen, and the proteins extracted for 1 h at 4° C. in 50 mM Tris-HCl buffer, 1% PVP25, 0.05% Triton X100, pH 7.5 in an amount of 4 ml of buffer per gram of fresh weight. After centrifugation, the concentration of protein in the supernatant was determined by the Bradford method.

Five micrograms of protein of each of the 9 extracts were deposited on nitrocellulose membrane in a "slot-blot" format, as well as a quantity of 50 ng of pure heliomicine which serves as positive control. The membrane was incubated for 1 h in 1% blocking buffer (Boehringer; ref 1 921 673) in TBS, and then incubated overnight at 4° C. with immunopurified antibodies directed against heliomicine, diluted, 1/2000 in TBS buffer with 0.05% Tween 20. After washing (TBS, 0.1 Tween 20 and 0.5% of blocking buffer), the membrane was incubated for 1 h at room temperature (TBS with 0.5% blocking buffer) with a goat antibody (diluted 1/50 000) directed specifically against rabbit inimunoglobulins and coupled to alkaline phosphatase (SIGMA A-3687). After washing (TBS, 0.1% Tween 20), the detection is made by adding a phosphatase substrate (BioRad ref 170-5012), and the revealing is obtained by radiography of the luminescent product on Amersham film (ECL).

The result of this experiment shows that 4 transgenic tobacco plants strongly express heliomicine. The signal in the other transgenic plants is weak or not significant compared with the wild-type control. The signal observed for the best plant is at the level of the positive control (50 ng of heliomicine), which indicates that in this plant, heliomicine represents by weight about 1% of the total proteins.

EXAMPLE V-1

Emulsifiable Concentrates

Example EC1

| | |
|---|---|
| active substance | 400 g/l |
| alkali metal dodecylbenzenesulphonate | 24 g/l |
| oxyethylated nonylphenol containing 10 molecules of ethylene oxide | 16 g/l |
| cyclohexanone | 200 g/l |
| aromatic solvent | qs 1 liter |

Example EC2

| | |
|---|---|
| active substance | 250 g |
| epoxidized vegetable oil | 25 g |
| mixture of alkylarylsulphonate and polyglycol ether and fatty alcohols | 100 g |
| dimethylformamide | 50 g |
| xylene | 575 g |

EXAMPLE V-2 Flowable

Example F 1

| | |
|---|---|
| active substance | 500 g |
| polyethoxylated tristyrylphenol phosphate | 50 g/l |
| polyethoxylated alkylphenol | 50 g |
| sodium carboxylate | 20 g |
| ethylene glycol | 50 g |
| organopolysiloxane oil (anti foam) | 1 g |
| polysaccharide | 1.5 g |
| water | 316.5 g |

EXAMPLE V-3

Wettable Powders (or Spraying Powders)

Example WP 1

| | |
|---|---|
| active substance | 50% |
| ethoxylated fatty alcohol (wetting agent) | 2.5% |
| ethoxylated phenylethylphenol (dispersing agent) | 5% |
| chalk (inert carrier) | 42.5% |

Example WP 2

| | |
|---|---|
| active substance | 10% |
| C13, branched type oxo synthetic alcohol ethoxylated with 8 to 10 ethylene oxide (wetting agent) | 0.75% |
| neutral calcium lignosulphonate (dispersing agent) | 12% |
| calcium carbonate (inert filler) | qs 100% |

Example WP 3

| | |
|---|---|
| active substance | 75% |
| wetting agent | 1.50% |
| dispersing agent | 8% |
| calcium carbonate (inert filler) | qs 100% |

Example WP 4

| | |
|---|---|
| active substance | 90% |
| ethoxylated fatty alcohol {wetting agent) | 4% |
| ethoxylated phenylethylphenol (dispersing agent) | 6% |

Example WP 5

| | |
|---|---|
| active substance | 50% |
| mixture of anionic and nonionic surfactants (wetting agent) | 2.5% |
| sodium lignosulphonate (dispersing agent) | 5% |
| kaolinic clay (inert carrier) | 42.5% |

EXAMPLE V-4

Dispersible Granules

Example DG 1

90% by weight of active substance and 10% of pearl urea are mixed in a mixer. The mixture is then ground in a toothed roll grinder. A powder is obtained which is wetted with about 8% by weight of water. The wet powder is extruded in a perforated roll extruder. Granules are obtained which are dried and then crushed and sieved so as to retain respectively only the granules having a size of between 150 and 2000 microns.

Example DG2

The following constituents are mixed in a mixer:

| | |
|---|---|
| active substance | 75% |
| wetting agent (sodium alkylnaphthalenesulphonate) | 2% |
| dispersing agent (sodium polynaphthalenesulphonate) | 8% |
| inert filler insoluble in water (kaolin) | 15% |

This mixture is granulated on a fluidized bed, in the presence of water, and then dried, crushed and sieved so as to obtain granules having a size of between 0.15 and 0.80 mm.

EXAMPLE V-5

Pharmaceutical Compositions

Example A

Tablets

Tablets containing 50 mg doses of active peptide having the following composition are prepared according to the usual technique:

| | |
|---|---|
| peptide heliomicine M1 | 50 mg |
| starch | 60 mg |
| lactose | 50 mg |
| magnesium stearate | 2 mg |

Example B

Injectable Solution

An injectable solution containing 20 mg of active peptide having the following composition is prepared:

| | |
|---|---|
| peptide heliomicine M 2 | 22.4 mg |
| distilled water | qs 2 cm$^3$ |

EXAMPLE VI

Stability of the Activity of Heliomicine

The stability of an antimicrobial peptide towards plant pro teases is an essential factor for obtaining a good level of expression and therefore of resistance to phytopathogens in transgenic plants. This stability is for example a critical point for an insect antimicrobial peptide such as cecropin B (Owens and Heutte, 1997, MPMI vol 10, No. 4, pp 525–528). We examined the stability of heliomicine and of its activity on a test phytopathogen (Botrytis cinerea) after incubation with crude extracts of 8 major crop plants (maize, wheat, barley, rape, soyabean, sunflower, tomato and tobacco). The leaves of these 8 species were ground at low temperature (liquid nitrogen) in a mortar, and then the powder was resuspended in the same volume of water. After centrifugation (10,000 g for 30 minutes), the supernatant was recovered and the protein concentration determined. This concentration was adjusted for the 8 extracts to 1 mg/ml by dilution with water and then these extracts were filtered sterilely (0.2 microns). One hundred microlitres of each extract (as well as a control with only water) were then added to 50 microlitres of a solution of heliomicine (containing 15 micrograms, as well as a control without peptide) in water. These mixtures were incubated at 30° C., one aliquot of 20 microlitres collected after 0 h, 1 h, 2 h, 4 h and 20 h and immediately frozen up to the test.

The test of antifungal activity was carried out at 25° C. in microplates by adding each aliquot to 80 microlitres of a fresh suspension of Botrytis cinerea spores (10,000 spores/ml in a solution of Potato Dextrose Broth (Difco, 12 g/l)). Visual reading of the results after 12 h and 24 h shows that there is no significant loss of antifungal activity of heliomicine even for the sample incubated for 20 h at 30° C., linked to the exposure of a crude extract of maize, wheat, barley, rape, soyabean, sunflower, tomato or tobacco. This result indicates a very high stability of heliomicine to plant proteases, and that the antifungal activity tested on Botrytis cinerea is not affected by the presence of crude plant extracts.

EXAMPLE VII

Production of Various Heliornicine Mutants: Single, Double, Triple and Quadruple Mutants The mutants below are prepared according to the method described in Example II by replacing some of the oligonucleotides 1 to 6 with other oligonucleotides chosen in order to introduce the mutations.

- heliomicine R48: replacement of the amino acid Glu48 of SEQ ID NO:1 with a basic amino acid, in particular an arginine (Arg48). By analogy with the sequence encoding the heliomicine having the sequence: SEQ ID NO:1, the codon GAA encoding Glu is replaced by the codon AGA encoding Arg. The oligonucleotides 19 and 20 are used as a replacement for the oligonucleotides 5 and 6 of Example II.

Oligo 19: 5' GATCCTTCGC TAACGTTAAC TGTTGGT-GTA GAACCTGATA GG 3' (SEQ ID NO:27)

Oligo 20: 5' TCGACCTATC AGGTTCTACA CCAA-CAGTTA ACGTTAGCGA AG 3' (SEQ ID NO:28)

- heliomicine L28L29: replacement of two basic amino acids Lys and Arg at position 28 and 29 of SEQ ID NO:1 with two hydrophobic amino acids, in particular two leucine amino acids (Leu28 and 29). By analogy with the sequence encoding the heliomicine having the sequence: SEQ ID NO:1, the part AAG-CGC encoding the peptide residue Lys-Arg is replaced by the sequence TTG-TTG encoding the peptide residue Leu-Leu. The oligonucleotides 21 and 22 are used as are placement for the oligonucleotides 3 and 4 of Example II.

Oligo 21: 5' CTAGTGACTG CAACGGCGAG TGCTTGT-TGC GC 3' (SEQ ID NO:29)

Oligo 22: 5' GCAACAAGCA CTCGCCGTTG CAGTCA 3' (SEQ ID NO:30)

- heliomicine L28L29R48: replacement of the two basic amino acids Lys and Arg at position 28 amd 29 SEQ ID NO:1 by two leucine amino acid residues and replacement of the amino acid Glu48 of SEQ ID NO:1 by the amino acid arginine (Arg48). The oligonucleotides 19 to 22 are used as a replacement for the oligonucleotides 3 to 6 according to Example II.

- heliomicine A24A25: replacement of the two amino acids Asn24 and Gly25 of SEQ ID NO:1 by two alanine amino acids (Ala24 and Ala25). By analogy with the sequence encoding the heliomicine of SEQ ID NO:1, the part AAC-GGC encoding the peptide residue Asn-Gly is replaced by the sequence GCT-GCT encoding Ala-Ala. The oligonucleotides 23 and 24 are used as a replacement for the oligonucleotides 3 and 4 of Example II.

Oligo 23: 5' CTAGTGACTG CGCTGCTGAG TGCAAGCGGC GC 3' (SEQ ID NO:31)

Oligo 24: 5' GCCGCTTGCA CTCAGCAGCG CAGTCA 3' (SEQ ID NO:32)

- heliomicine A6A7A8A9: replacement of the amino acids Asp6-Lys7-Leu8-Ile9 of SEQ ID NO:1 by 4 alanine amino acids (Ala). By analogy with the sequence encoding the heliomicine of SEQ ID NO:1, the part GAC-AAG-TTG-ATT encoding the peptide residue Asp-Lys-Leu-Ile is replaced by the sequence GCT-GCT-GCT-GCT encoding the peptide residue Ala-Ala-Ala-Ala. The oligonucleotides 25 and 26 are used as a replacement for the oligonucleotide 1 of Example II and the oligonucleotides 27 and 28 as a replacement for the oligonucleotide 2.

Oligo 25: 5' AGCTTGGATA AAAGAGCTGC TGCTGCTGGT AGCTGTGTTT 3' (SEQ ID NO:33)

Oligo 26: 5' GGGGCGCCG TCAACTACA 3' (SEQ ID NO:34)

Oligo 27: 5' CTAGTGTAGT TGACGGCGCC CC 3' (SEQ ID NO:35)

Oligo 28: 5' AAACACAGCT ACCAGCAGCA GCAGCTCTTT TATCCA 3' (SEQ ID NO:36)

- heliomicine A24A25L28L29: Two oligonucleotides (sense and antisense) were necessary to compensate for the absence of a restriction site between the sequence encoding the peptide residue consisting of the two amino acids Asn24-Gly25 and the sequence encoding the peptide residue consisting of the two amino acids Lys28-Arg29 of the heliomicine of SEQ ID NO:1. The two oligonucleotide sequences 29 and 30 replace respectively the two oligonucleotide sequences 3 and 4 of Example II.

Oligo 29: 5' CTAGTGACTG CGCTGCTGAG TGCTTGT-TGC GC 3' (SEQ ID NO:37)

Oligo 30: 5' GCAACAAGCA CTCAGCAGCG CAGTCA 3' (SEQ ID NO:38)

Production of Mutated Heliomicine on the Semipreparative Scale

The various mutants of heliomicine are prepared and purified in the following manner. One of the transformed yeast clones expressing the mutated heliomicine was cultured at 29° C. for 48 h in 50 ml of selective medium. This preculture was then used to inoculate 21 of selective medium and the culture was carried out for 48 h 29° C. The yeasts were removed by centrifugation (4000 g, 30 min, 4° C.). The supernatant was acidified to pH 3.5 with acetic acid, subjected to a second centrifugation (4000 g, 30 min, 54° C.) before a first solid phase extraction step.

- first solid phase extraction step on are versed phase gel: the acidified supernatant is deposited on a C18 reversed phase Sep-Pak Vac 35 cc cartridge (Waters Associates, 10 g of phase) equilibrated with acidified water (0.05% TFA). The hydrophilic molecules were removed by washing with acidified water followed by washing with a 15% acetonitrile solution prepared in 0.05% TFA. The elution of the peptide was carried out with a 60% acetonitrile solution prepared in 0.05% TFA. The fraction eluted with 60% acetonitrile was freeze-dried and then reconstituted in sterile ultra pure water before being subjected to the first purification step.

- second solid phase extraction step on a cation-exchange gel: the 60% prepurified fraction containing the mutated heliomicine was reconstituted in 25 mM ammonium acetate solution, pH 3.4. This sample was deposited on a CM cation-exchange Sep-Pak Vac 35 cc cartridge (Waters Associates, 10 g of phase) equilibrated with 25 mM ammonium acetate, pH 3.4. The mutated heliomicine is eluted using a 1 M sodium chloride (NaCl) solution prepared in 25 mM ammonium acetate, pH 3.4. The 1 M NaCl fraction containing the mutated heliomicine is recovered, dried under vacuum, reconstituted with 20 ml of acidified ultrapure water (1% TFA). The mutated heliomicine is then purified by reversed-phase HPLC.

- last purification step by HPLC: the mutated heliomicine was purified to homogeneity by chromatography on a preparative reversed-phase column Aquapo re RP-300 C8 (Brownlee™, 220×10 mm, 300 Å), using a biphasic linear gradient of acetonitrile from 2% to 23% over 10 min and from 23% to 33% over 80 min in 0.05% TFA at constant flow rate of 2.5 ml/min. The fraction collected is dried under vacuum, reconstituted with ultrapure water and analyzed by MALDI mass spectrometry in order to verify the purity and the identity. The different mutated heliomicines were analyzed for their antifungal activity under the conditions described for the reference heliomicine against the following strains: *Neurospora crassa, Fusarium culmorum* and *Nectria haematococca*. The activity of the mutants of heliomicine was also evaluated against bacteria. The experimental conditions used are described below.

Test of Activity in Vitro: Measurement of the Antibacterial and Antifungal Activity by Microspectrophotometry This methodology was used for the determination of the activity spectrum of the peptide and of the minimum inhibitory concentration (MIC) at which the mutated peptide is active. The MIC was expressed as the concentration range [a]–[b] where [a] was the minimum concentration where an onset of growth is observed and [b] the concentration for which no growth was observed. Examples of specific activity of the mutated heliomicine, with respect to bacteria and filamentous fungi, are given in Table 3.

The antibacterial activity was detected by a test of inhibition of growth in liquid medium. The bacteria to be tested were suspended in a nutrient medium of the "Poor Broth" type. Preferably, a 1% bactotryptone solution supplemented with 1% NaCl by weight/volume, prepared in demineralized water, is used. 10 µl of each fraction to be analyzed are deposited in microtiter plates in the presence of 90 µl of culture medium containing the bacteria (at a final concentration equivalent to 1 m OD at 600 nm). The incubation was carried out at 25° C. for 12 to 24 hours. The bacterial growth was measured by monitoring absorbance at 600 nm with the aid of a microtiter plate reader spectrophotometer.

- bacteria tested: *Bacillus megaterium* (collection de Institut Pasteur), *Micrococcus luteus* (collection de l'Institut Pasteur), *Staphylococcusaureus* (H. Monteil, Institute of bacteriology, Strasbourg), *Aerococcus viridans* (H. Monteil, Institute of bacteriology, Strasbourg), and *Escherichia coli* D22 (P.L. Boquet, Centre for nuclear studies, Sac lay).

TABLE 3

Activity of some mutated heliomicines against filamentous fungi and bacteria

| Micro-organisms | MIC for the mutants of heliomicine (μm) | | | | |
|---|---|---|---|---|---|
| | L28L29 | R48 | L28L29R48 | A6A7A8A9 | Helio |
| Fungi | | | | | |
| Neurospora crassa | 0.8–1.6 | 0.4–0.8 | 0.8–1.6 | 1.6–3.1 | 0.1–0.2 |
| Fusarium culmorum | 3.1–6.2 | 0.4–0.8 | 0.8–1.6 | 3.1–6.2 | 0.2–0.4 |
| Nectria haematococca | 3.1–6.2 | 0.4–0.8 | 0.8–1.6 | ND | 0.4–0.8 |
| Bacteria | | | | | |
| Bacillus megaterium | 50–100 | ND | ND | 6.2–12.5 | ND |
| Micrococcus luteus | 12.5–25 | 25–50 | ND | ND | ND |
| Staphylococcus aureus | ND | ND | ND | ND | ND |
| Aerococcus viridans | ND | ND | ND | 12.5–25 | ND |
| Escherichia coli D22 | ND | ND | ND | ND | ND |

ND: no activity detected

EXAMPLE VIII

Study of Acute Toxicity

Groups of 4 female mice were treated by intravenous injection of solutions of heliomicine (SEQ ID NO:2) in saline solution at doses of 1 and 10 mg/kg. Corresponding solutions of aprotinine as negative control (no effect for the two doses) and mellitin as positive control (100% mortality at 5 days at 10 mg, significant effects at 5 days at 1 mg). No toxicity was demonstrated for the heliomicine solutions at the two doses injected.

References

Ausubel, F. A. et al.(eds. Greene). Current Protocols in Molecular Biology. Publ. Wiley & Sons.
Bevan, M. et al. (1983). Nuc. Acids Res. 11:369–385.
Carrington and Freed (1990). J. Virol. 64: 1590–1597.
Ehret-Sabatier et al.(1996). The Journal of Biological Chemistry, 271,47, 29537–29544.
Horsch et al.(1985). Science 227: 1229–1231.
Jefferson et al. (1987). EMBO J. 6: 3901–3907.
Komari et al.(1986). J. Bacteriol. 166: 88–94.
Rothstein et al. (1981). Cold Spring Harb. Symp. Quant. Biol. 45: 99–105.
Stalker et al. (1988). J. Biol. Chem. 263: 6310–6314.
Odell, J. T. et al. (1985). Nature 313: 810–812.

---

What is claimed is:

1. An isolated peptide comprising the peptide sequence of formula (I),

Xaa-Cys-Xab-Cys-Xac-Cys-Xad-Cys-Xae-Cys-Xaf-Cys-Xag (SEQ ID NO:39)     (1)

in which;
- Xaa represents an N-terminal $NH_2$- (amino) moiety or a peptide fragment consisting of from 1 to 10 amino acid residues, wherein at least one of said residues basic amino acid residue;
- Xab represents 10 amino acid residues;
- Xac represents 3 amino acid residues, comprising at least one acidic amino acid residue;
- Xad represents the peptide sequence, -Lys-Arg-Arg-Gly-Tyr-Lys-Gly-Gly-His-(SEQ ID NO:41);
- Xae represents the peptide sequence -Gly-Xae'-Asn-(SEQ ID NO:44), in which Xae' represents 5 amino acid residues;
- Xaf represents the amino acid -Trp-; and
- Xag represents a C-terminal —COOH (carboxyl) moiety or a peptide fragment consisting of from 1 to 2 amino acid residues, wherein said peptide has an antifungal activity.

2. The peptide of claim 1, wherein Xad comprises 1, 2, 3 or 4 amino acid residues.

3. The peptide of claim 1, wherein the basic amino acids are selected from the group consisting of lysine, arginine and homoarginine.

4. The peptide of claim 1, wherein Xac represents the peptide sequence -Asn-Xac'-Xac"-, in which Xac' represents one amino acid residue, and $X_{ac}"$ represents one acidic amino acid residue.

5. The peptide of claim 1, characterized in that the acidic amino acids are chosen from glutamic acid (Glu) or aspartic acid (Asp).

6. The peptide of claim 1, wherein Xac represents the peptide sequence -Asn-Gly-Glu-(SEQ ID NO:50).

7. The peptide of claim 1, wherein

Xaa represents the peptide sequence Xaa'-Gly-Xaa"-(SEQ ID NO:42), in which Xaa' represents an N-terminal $NH_2$- (amino) moiety or a peptide fragment consisting of from 1 to 8 amino acid residues, and Xaa" represents one acidic amino acid residue; and/or Xab represents the peptide sequence -Val-Xab'-Asp-(SEQ ID NO:43) in which Xab' represents from 0 to 8 amino acid residues; and/or Xag represents the peptide sequence -Glu-Xag' (SEQ ID NO:45), in which Xag' represents a C-terminal —COOH (carboxyl) moiety or one amino acid residue.

8. The peptide of claim 1, wherein

Xaa represents the peptide sequence NH$_2$-Asp-Lys-Leu-Ile-Gly-Ser- (SEQ ID NO:46), in which NH$_2$— represents an N-terminal NH$_2$— (amino) moiety; and/or Xab represents the peptide sequence -Val-Trp-Gly-Ala-Val-Asn-Tyr-Thr-Ser-Asp- (SEQ ID NO:47); and/or Xae represents the peptide sequence -Gly-Ser-Phe-Ala-Asn-Val-Asn (SEQ ID NO:48); and/or Xag represents the peptide sequence -Glu-Thr-COOH, wherein —COOH represents a C-terminal carboxyl moiety.

9. The peptide of claim 1, wherein said peptide has the amino acid sequence encoded by SEQ ID NO:2.

10. The peptide of claim 1, wherein said peptide comprises at either of its ends (N-terminus and C-terminus), or at both ends, amino acid residues necessary for its expression and targeting to a specific compartment of the host organism.

11. The peptide of claim 1, wherein the cysteine residues of the peptide of formula (I) form at least one intramolecular disulfide bridge.

12. The peptide of claim 11, wherein said peptide comprises disulfide bridges established between the first and fourth cysteine residues, the second and fifth cysteine residues, and the third and sixth cysteine residues of the peptide sequence of formula (I).

13. The peptide of claim 1, wherein Xaa represents an N-terminal NH$_2$— (amino) moiety or from 1 to 6 amino acid residues.

14. The peptide of claim 1, wherein Xac comprises one acidic amino acid residue.

15. The peptide of claim 1, wherein Xaa represents the peptide sequence Xaa'-Gly-Xaa"-in which Xaa' represents an N-terminal NH$_2$— (amino) moiety or a peptide fragment consisting of from 1 to 5 amino acid residues, and Xaa" represents an amino acid selected from the group consisting of Leu, Ile, Val, Pro, Ser and Thr.

16. The peptide of claim 1, wherein Xab represents the peptide sequence -Val-Xab'-Asp- (SEQ ID NO:43) in which Xab' represents 8 amino acid residues.

17. The peptide of claim 1, wherein Xag represents the peptide sequence -Glu-Xag' in which Xag' represents a C-terminal —COOH (carboxyl) moiety or one amino acid residue.

18. A fusion peptide comprising the peptide of claim 1.

19. The fusion peptide of claim 18, wherein the peptide comprises a signal peptide or a transit peptide.

20. The fusion peptide of claim 19, wherein the transit peptide is selected from the group consisting of the signal peptide encoded by the tobacco PR-1α a gene, the signal peptide present at the N-terminal of the precursor of factor Mat alpha 1, and the signal peptide encoded by the maize polygalacturonase PG1 gene.

21. A composition which comprises the peptide of claim 1 and an appropriate vehicle.

22. A method of preparing the peptide of claim 1, comprising culturing a transformed organism that contains a nucleic acid encoding said peptide in an appropriate culture medium; extracting said peptide; and totally or partially purifying said peptide.

* * * * *

SEQUENCE LISTING

```
<160> NUMBER OF SEQ ID NOS: 53

<210> SEQ ID NO 1
<211> LENGTH: 147
<212> TYPE: DNA
<213> ORGANISM: Artificial Sequence
<220> FEATURE:
<223> OTHER INFORMATION: Synthetic oligonucleotide

<400> SEQUENCE: 1
agcttggata aagagacaa gttgattggc agctgtgttt ggggcgccgt caactacact      60
agtgactgca acggcgagtg caagcgccgc ggttacaagg gtggccattg tggatccttc    120
gctaacgtta actgttggtg tgaaacc                                        147

<210> SEQ ID NO 2
<211> LENGTH: 169
<212> TYPE: DNA
<213> ORGANISM: Artificial Sequence
<220> FEATURE:
<223> OTHER INFORMATION: Synthetic oligonucleotide

<400> SEQUENCE: 2
gataagctta tcggttcctg cgtgtggggt gctgtgaact acacttccga ttgcaacggt     60
gagtgcaaga ggagggggtta caaggtggt cactgcggtt ccttcgctaa cgtgaactgc   120
tggtgcgaga cttgagagct cggcgaggcg aacgtgtcga cggatccgg                169

<210> SEQ ID NO 3
<211> LENGTH: 261
<212> TYPE: DNA
<213> ORGANISM: Artificial Sequence
<220> FEATURE:
<223> OTHER INFORMATION: Synthetic oligonucleotide
```

<400> SEQUENCE: 3

```
ccatgggttt cgtgcttttc tctcagcttc catctttcct tcttgtgtct actcttcttc    60
tttccttgt gatctctcac tcttgccgtg ccgataagct tatcggttcc tgcgtgtggg    120
gtgctgtgaa ctacacttcc gattgcaacg tgagtgcaa gaggagggt tacaagggtg    180
gtcactgcgg ttccttcgct aacgtgaact gctggtgcga gacttgagag ctcggcgagg    240
cgaacgtgtc gacggatccg g                                              261
```

<210> SEQ ID NO 4
<211> LENGTH: 120
<212> TYPE: DNA
<213> ORGANISM: Artificial Sequence
<220> FEATURE:
<223> OTHER INFORMATION: Synthetic oligonucleotide

<400> SEQUENCE: 4

```
gcgtcgacgc gatgggtttc gtgcttttct ctcagcttcc atctttcctt cttgtgtcta    60
ctcttcttct tttccttgtg atctctcact cttgccgtgc tggagacgcg aattcacaca   120
```

<210> SEQ ID NO 5
<211> LENGTH: 75
<212> TYPE: DNA
<213> ORGANISM: Artificial Sequence
<220> FEATURE:
<223> OTHER INFORMATION: Synthetic oligonucleotide

<400> SEQUENCE: 5

```
gcgtcgacgc gatgggtttc gtgcttttct ctcagcttcc atctttcctt cttgtgtcta    60
ctcttcttct tttcc                                                     75
```

<210> SEQ ID NO 6
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 6

```
tcgccggcac ggcaagagta agagatcaca aggaaaagaa gaagagtaga cacaagaagg    60
aaagatggaa gc                                                        72
```

<210> SEQ ID NO 7
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 7

```
gataagctta tcggttcctg cgtgtgggt gctgtgaact acacttccga ttgcaacggt    60
gagtgcaaga ggagggtta                                                 80
```

<210> SEQ ID NO 8
<211> LENGTH: 109
<212> TYPE: DNA
<213> ORGANISM: Artificial Sequence
<220> FEATURE:
<223> OTHER INFORMATION: Synthetic oligonucleotide

<400> SEQUENCE: 8

```
ccggatccgt cgacacgttc gcctcgccga gctctcaagt ctcgcaccag cagttcacgt    60
tagcgaagga accgcagtga ccaccttgt aaccctcct cttgcactc                 109
```

<210> SEQ ID NO 9
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 9

```
agggccccct agggtttaaa cggccagtca ggccgaattc gagctcggta cccggggatc    60
ctctagagtc gacctgcagg catgc                                         85
```

<210> SEQ ID NO 10
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 10

```
ccctgaacca ggctcgaggg cgcgccttaa ttaaaagctt gcatgcctgc aggtcgactc    60
tagagg                                                              66
```

<210> SEQ ID NO 11
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 11

```
ccggccagtc aggccacact taattaagtt taaacgcggc cccggcgcgc ctaggtgtgt    60
gctcgagggc ccaacctcag tacctggttc agg                                93
```

<210> SEQ ID NO 12
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 12

```
ccggcctgaa ccaggtactg aggttgggcc ctcgagcaca cacctaggcg cgccggggcc    60
gcgtttaaac ttaattaagt gtggcctgac tgg                                93
```

<210> SEQ ID NO 13
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 13

```
ggtctagaat ggcctgcacc aacaacgcca tgagggccct cttcctcctc              50
```

<210> SEQ ID NO 14
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 14
ccgaattcgg cgccgtgcac gatgcagaag agcacgagga ggaagagggc         50

<210> SEQ ID NO 15
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 15
tctagaatgg cctgcaccaa caacgccatg agggccctct tcctcctcct gctcttctgc    60
atcgtgcacg gcgccgaatt c                                             81

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
gataagctta tcggttcctg cgtg                                          24

<210> SEQ ID NO 17
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 17
ggctcgagtc aagtctcgca ccagcagttc ac                                 32

<210> SEQ ID NO 18
<211> LENGTH: 213
<212> TYPE: DNA
<213> ORGANISM: Artificial Sequence
<220> FEATURE:
<223> OTHER INFORMATION: Synthetic oligonucleotide

<400> SEQUENCE: 18
tctagaatgg cctgcaccaa caacgccatg agggccctct tcctcctcct gctcttctgc    60
atcgtgcacg gcgataagct tatcggttcc tgcgtgtggg gtgctgtgaa ctacacttcc   120
gattgcaacg gtgagtgcaa gaggagggt tacaagggtg gtcactgcgg ttccttcgct    180
aacgtgaact gctggtgcga gacttgactc gag                                213

<210> SEQ ID NO 19
<211> LENGTH: 838
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: promoter
<222> LOCATION: (7)...(532)
<220> FEATURE:
<221> NAME/KEY: misc_structure
<222> LOCATION: (533)...(568)
<220> FEATURE:
<221> NAME/KEY: terminator
<222> LOCATION: (569)...(832)

<400> SEQUENCE: 19

-continued

```
aagcttccag aaggtaatta tccaagatgt agcatcaaga atccaatgtt tacgggaaaa      60
actatggaag tattatgtga gctcagcaag aagcagatca atatgcggca catatgcaac     120
ctatgttcaa aaatgaagaa tgtacagata caagatccta tactgccaga atacgaagaa     180
gaatacgtag aaattgaaaa agaagaacca ggcgaagaaa agaatcttga agacgtaagc     240
actgacgaca acaatgaaaa gaagaagata aggtcggtga ttgtgaaaga gacatagagg     300
acacatgtaa ggtggaaaat gtaagggcgg aaagtaacct tatcacaaag gaatcttatc     360
ccccactact tatccttta tattttccg tgtcatttt gcccttgagt tttcctatat         420
aaggaaccaa gttcggcatt tgtgaaaaca agaaaaaatt tggtgtaagc tattttcttt     480
gaagtactga ggatacaact tcagagaaat ttgtaagttt gtagatctcg attctagaag     540
gcctgaattc gagctcggta ccggatccaa ttcccgatcg ttcaaacatt tggcaataaa     600
gtttcttaag attgaatcct gttgccggtc ttgcgatgat tatcatataa tttctgttga     660
attacgttaa gcatgtaata attaacatgt aatgcatgac gttatttatg agatgggttt     720
ttatgattag agtcccgcaa ttatacattt aatacgcgat agaaaacaaa atatagcgcg     780
caaactagga taaattatcg cgcgcggtgt catctatgtt actagatcgg ggatcgat      838
```

<210> SEQ ID NO 20
<211> LENGTH: 1036
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: promoter
<222> LOCATION: (7)...(532)
<220> FEATURE:
<221> NAME/KEY: CDS
<222> LOCATION: (539)...(736)
<220> FEATURE:
<221> NAME/KEY: terminator
<222> LOCATION: (767)...(1030)

<400> SEQUENCE: 20

```
aagcttccag aaggtaatta tccaagatgt agcatcaaga atccaatgtt tacgggaaaa      60
actatggaag tattatgtga gctcagcaag aagcagatca atatgcggca catatgcaac     120
ctatgttcaa aaatgaagaa tgtacagata caagatccta tactgccaga atacgaagaa     180
gaatacgtag aaattgaaaa agaagaacca ggcgaagaaa agaatcttga agacgtaagc     240
actgacgaca acaatgaaaa gaagaagata aggtcggtga ttgtgaaaga gacatagagg     300
acacatgtaa ggtggaaaat gtaagggcgg aaagtaacct tatcacaaag gaatcttatc     360
ccccactact tatcctttta tattttccg tgtcatttt gcccttgagt tttcctatat        420
aaggaaccaa gttcggcatt tgtgaaaaca agaaaaaatt tggtgtaagc tattttcttt     480
gaagtactga ggatacaact tcagagaaat ttgtaagttt gtagatctcg attctaga       538
```

```
atg gcc tgc acc aac aac gcc atg agg gcc ctc ttc ctc ctc gtg ctc      586
Met Ala Cys Thr Asn Asn Ala Met Arg Ala Leu Phe Leu Leu Val Leu
  1               5                  10                  15 ttc tgc atc gtg cac ggc gat aag ctt atc ggt tcc tgc gtg tgg ggt      634
Phe Cys Ile Val His Gly Asp Lys Leu Ile Gly Ser Cys Val Trp Gly
              20                  25                  30 gct gtg aac tac act tcc gat tgc aac ggt gag tgc aag agg agg ggt      682
Ala Val Asn Tyr Thr Ser Asp Cys Asn Gly Glu Cys Lys Arg Arg Gly
          35                  40                  45 tac aag ggt ggt cac tgc ggt tcc ttc gct aac gtg aac tgc tgg tgc      730
Tyr Lys Gly Gly His Cys Gly Ser Phe Ala Asn Val Asn Cys Trp Cys
```

```
Tyr Lys Gly Gly His Cys Gly Ser Phe Ala Asn Val Asn Cys Trp Cys
 50                  55                  60 gag act tgactcgagg gggggcccgg taccggatcc aattcccgat cgttcaaaca       786
Glu Thr
 65 tttggcaata aagtttctta agattgaatc ctgttgccgg tcttgcgatg attatcatat   846 aatttctgtt gaattacgtt aagcatgtaa taattaacat gtaatgcatg acgttattta   906 tgagatgggt ttttatgatt agagtcccgc aattatacat ttaatacgcg atagaaaaca   966 aaatatagcg cgcaaactag gataaattat cgcgcgcggt gtcatctatg ttactagatc   1026 ggggatcgat                                                          1036

<210> SEQ ID NO 21
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 21
agcttggata aagagacaa gttgattggc agctgtgttt ggggcgccgt ca             52

<210> SEQ ID NO 22
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 22
agtgtagttg acggcgcccc aaacacagct gccaatcaac ttgtctcttt tatcca        56

<210> SEQ ID NO 23
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 23
actacactag tgactgcaac ggcgagtgca agcgccgcgg ttacaagggt gg             52

<210> SEQ ID NO 24
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 24
cacaatggcc acccttgtaa ccgcggcgct tgcactcgcc gttgcagtca ct             52

<210> SEQ ID NO 25
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 25
ccattgtgga tccttcgcta acgttaactg ttggtgtgaa acctgatagg tcgaca        56

<210> SEQ ID NO 26
```

```
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 26
gatctgtcga cctatcaggt ttcacaccaa cagttaacgt tagcgaagga tc        52

<210> SEQ ID NO 27
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 27
gatccttcgc taacgttaac tgttggtgta gaacctgata gg                   42

<210> SEQ ID NO 28
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 28
tcgacctatc aggttctaca ccaacagtta acgttagcga ag                   42

<210> SEQ ID NO 29
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 29
ctagtgactg caacggcgag tgcttgttgc gc                              32

<210> SEQ ID NO 30
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 30
gcaacaagca ctcgccgttg cagtca                                     26

<210> SEQ ID NO 31
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 31
ctagtgactg cgctgctgag tgcaagcggc gc                              32

<210> SEQ ID NO 32
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 32
```

```
gccgcttgca ctcagcagcg cagtca                                        26

<210> SEQ ID NO 33
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 33
agcttggata aaagagctgc tgctgctggt agctgtgttt                         40

<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 34
ggggcgccgt caactaca                                                 18

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
ctagtgtagt tgacggcgcc cc                                            22

<210> SEQ ID NO 36
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 36
aaacacagct accagcagca gcagctcttt tatcca                             36

<210> SEQ ID NO 37
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 37
ctagtgactg cgctgctgag tgcttgttgc gc                                 32

<210> SEQ ID NO 38
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 38
gcaacaagca ctcagcagcg cagtca                                        26

<210> SEQ ID NO 39
<211> LENGTH: 51
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(10)
<223> OTHER INFORMATION: region of variable length from 1 to 10 amino
      acids where Xaa = any amino acid
<220> FEATURE:
<221> NAME/KEY: VARIANT
<222> LOCATION: (12)...(21)
<223> OTHER INFORMATION: region of variable length from 1 to 10 amino
      acids where Xaa = any amino acid
<220> FEATURE:
<221> NAME/KEY: VARIANT
<222> LOCATION: (23)...(25)
<223> OTHER INFORMATION: Xaa = any amino acid
<220> FEATURE:
<221> NAME/KEY: VARIANT
<222> LOCATION: (27)...(35)
<223> OTHER INFORMATION: region of variable length from 1 to 9 amino
      acids where Xaa = any amino acid
<220> FEATURE:
<221> NAME/KEY: VARIANT
<222> LOCATION: (37)...(43)
<223> OTHER INFORMATION: region of variable length from 1 to 7 amino
      acids where Xaa = any amino acid
<220> FEATURE:
<221> NAME/KEY: VARIANT
<222> LOCATION: (45)...(45)
<223> OTHER INFORMATION: Xaa = any amino acid
<220> FEATURE:
<221> NAME/KEY: VARIANT
<222> LOCATION: (47)...(51)
<223> OTHER INFORMATION: region of variable length from 1 to 5 amino
      acids where Xaa = any amino acid

<400> SEQUENCE: 39

Xaa Xaa Xaa Xaa Xaa Xaa Xaa Xaa Xaa Xaa Cys Xaa Xaa Xaa Xaa Xaa
 1               5                  10                  15

Xaa Xaa Xaa Xaa Xaa Cys Xaa Xaa Xaa Cys Xaa Xaa Xaa Xaa Xaa Xaa
            20                  25                  30

Xaa Xaa Xaa Cys Xaa Xaa Xaa Xaa Xaa Xaa Cys Xaa Cys Xaa Xaa
        35                  40                  45

Xaa Xaa Xaa
    50

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)...(2)
<223> OTHER INFORMATION: Xaa = any basic amino acid
<220> FEATURE:
<221> NAME/KEY: VARIANT
<222> LOCATION: (3)...(7)
<223> OTHER INFORMATION: region of variable length from 0 to 5 amino
      acids where Xaa = any amino acid
<220> FEATURE:
<221> NAME/KEY: VARIANT
<222> LOCATION: (1)...(9)
<223> OTHER INFORMATION: Xaa = Any Amino Acid

<400> SEQUENCE: 40

Lys Xaa Xaa Xaa Xaa Xaa Xaa Gly His
 1               5

<210> SEQ ID NO 41
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Lys Arg Arg Gly Tyr Lys Gly Gly His
 1               5

<210> SEQ ID NO 42
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(9)
<223> OTHER INFORMATION: region of variable length from 0 to 9 amino
      acids where Xaa = any amino acid
<220> FEATURE:
<221> NAME/KEY: VARIANT
<222> LOCATION: (11)...(11)
<223> OTHER INFORMATION: Xaa = any amino acid
<220> FEATURE:
<221> NAME/KEY: VARIANT
<222> LOCATION: (1)...(11)
<223> OTHER INFORMATION: Xaa = Any Amino Acid

<400> SEQUENCE: 42

Xaa Xaa Xaa Xaa Xaa Xaa Xaa Xaa Xaa Gly Xaa
 1               5                  10

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)...(9)
<223> OTHER INFORMATION: region of variable length from 0 to 8 amino
      acids where Xaa = any amino acid
<220> FEATURE:
<221> NAME/KEY: VARIANT
<222> LOCATION: (1)...(10)
<223> OTHER INFORMATION: Xaa = Any Amino Acid

<400> SEQUENCE: 43

Val Xaa Xaa Xaa Xaa Xaa Xaa Xaa Xaa Asp
 1               5                  10

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)...(6)
<223> OTHER INFORMATION: region of variable length from 0 to 5 amino
      acids where Xaa = any amino acid
<220> FEATURE:
<221> NAME/KEY: VARIANT
<222> LOCATION: (1)...(7)
<223> OTHER INFORMATION: Xaa = Any Amino Acid

<400> SEQUENCE: 44

Gly Xaa Xaa Xaa Xaa Xaa Asn
```

<210> SEQ ID NO 45
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)...(5)
<223> OTHER INFORMATION: region of variable length from 0 to 4 amino
      acids where Xaa = any amino acid
<220> FEATURE:
<221> NAME/KEY: VARIANT
<222> LOCATION: (1)...(5)
<223> OTHER INFORMATION: Xaa = Any Amino Acid

<400> SEQUENCE: 45

Glu Xaa Xaa Xaa Xaa
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide

<400> SEQUENCE: 46

Asp Lys Leu Ile Gly Ser
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide

<400> SEQUENCE: 47

Val Trp Gly Ala Val Asn Tyr Thr Ser Asp
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

Gly Ser Phe Ala Asn Val Asn
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Leu Leu Arg Gly Tyr Lys Gly Gly His
1               5

<210> SEQ ID NO 50
<211> LENGTH: 3

```
<212> TYPE: PRT
<213> ORGANISM: Artificial Sequence
<220> FEATURE:
<223> OTHER INFORMATION: Synthetic peptide

<400> SEQUENCE: 50

Asn Gly Glu
 1

<210> SEQ ID NO 51
<211> LENGTH: 3
<212> TYPE: PRT
<213> ORGANISM: Artificial Sequence
<220> FEATURE:
<223> OTHER INFORMATION: Synthetic peptide

<400> SEQUENCE: 51

Ala Ala Glu
 1

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide

<400> SEQUENCE: 52

Ala Ala Ala Ala Gly Ser
 1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic peptide

<400> SEQUENCE: 53

Ser Leu Asp Lys Arg
 1               5
```